United States Patent [19]

Yang et al.

[11] Patent Number: 5,576,022
[45] Date of Patent: Nov. 19, 1996

[54] CONTROLLED RELEASE TACRINE DRUG DELIVERY SYSTEMS AND METHODS FOR PREPARING SAME

[75] Inventors: S. Shirley Yang, Succasunna; Wayne Boisvert, Randolph; Nouman A. Muhammad, Long Valley; Jay Weiss, East Brunswick, all of N.J.

[73] Assignee: Warner Lambert Company, Morris Plains, N.J.

[21] Appl. No.: 422,019

[22] Filed: Apr. 12, 1995

Related U.S. Application Data

[63] Continuation of Ser. No. 96,140, Jul. 22, 1993, abandoned.
[51] Int. Cl.$^6$ ........................................ A61K 9/24
[52] U.S. Cl. ........................................ 424/472
[58] Field of Search ........................ 424/473, 480, 424/472

[56] References Cited

U.S. PATENT DOCUMENTS

| | | | |
|---|---|---|---|
| 3,247,066 | 4/1966 | Milosovich, Jr. et al. | 424/495 |
| 4,173,626 | 11/1979 | Dempski et al. | 424/462 |
| 4,250,166 | 2/1981 | Maekawa et al. | 424/419 |
| 4,728,512 | 3/1988 | Mehta et al. | 424/458 |
| 4,794,001 | 12/1988 | Mehta et al. | 424/458 |
| 4,839,364 | 6/1989 | Shutske et al. | 514/290 |
| 4,904,476 | 2/1990 | Mehta et al. | 424/456 |
| 5,013,741 | 5/1991 | Shutske et al. | 514/290 |
| 5,085,865 | 2/1992 | Nayak et al. | 424/480 |
| 5,133,974 | 7/1992 | Paradissis et al. | 424/480 |
| 5,229,135 | 7/1993 | Philippon et al. | 424/480 |

FOREIGN PATENT DOCUMENTS

| | | | |
|---|---|---|---|
| 377518A | 5/1990 | European Pat. Off. | A61K 9/52 |
| 2749745 | 11/1977 | Germany | A61K 31/415 |
| 3909689 | 3/1989 | Germany | A61K 9/24 |
| 3922167 | 1/1991 | Germany | A61K 9/50 |
| 2047096 | 4/1980 | United Kingdom | A61K 9/16 |
| 8605393A | 11/1985 | WIPO | A61K 9/16 |
| 9215285 | 9/1992 | WIPO | |
| 9214443 | 9/1992 | WIPO | A61K 9/113 |
| 9301804 | 2/1993 | WIPO | A61K 9/16 |

OTHER PUBLICATIONS

J. Skelly, G. Amidon, W. Barr et al, "In vitro and in vivo testing and correlation for Oral Controlled/ modified–release dosage forms". *Pharmaceutical Research*, vol. 7, No. 9 pp. 975–982 (1990).

(List continued on next page.)

*Primary Examiner*—Peter F. Kulkosky
*Attorney, Agent, or Firm*—Michael J. Atkins

[57] ABSTRACT

The present invention pertains to controlled release tacrine drug delivery systems comprising an immediate release composition and a sustained release composition wherein (1) the immediate release composition comprises in percentages by weight of the immediate release composition: (A) immediate release pellets comprising: (a) nonpareil seeds in an amount from about 25% to about 75%; (b) tacrine in an amount from about 10% to about 80%; and (c) a binding agent in an amount from about 1% to about 10%; and (B) a sealing layer over the immediate release pellets comprising: (a) a sealing agent in an amount up to about 6%, and (b) a first plasticizing agent in an amount up to about 5%; and (2) the sustained release composition comprises in percentages by weight of the sustained release composition; (A) the immediate release composition; and (B) a sustaining layer over the immediate release composition comprising; (a) a water-insoluble polymer in an amount from about 40% to about 90%; (b) a water-soluble polymer in an amount up to about 10%; and (c) a second plasticizing agent in an amount up to about 10%; wherein the sustaining layer and the immediate release composition are present in the sustained release composition in a ratio by weight from about 1:9 to about 4:6, respectively, and the immediate release composition and the sustained release composition are present in the drug delivery system in a ratio by weight from about 0.01:1 to about 1:1, respectively.

20 Claims, 21 Drawing Sheets

OTHER PUBLICATIONS

A. R. Hunter, "Tetrahydroaminacrine in Anesthesia". *Br. J. Anesth.*, 37:505–513 (1965).

T. Gordh, A. Wahlin, "Potentiation of the neuromuscular effect of succinylcholine by tetrahydroamineacridine". *Acta Anaesthiol Scand.*, 5:51–55 (1961).

W. K. Summers, L. V. Majovski, G. M. Marsch, K. Tachiki, and A. Kling, "Oral tetrahydroaminoacridine in long term treatment of senile dementia". *N. Engl. J. Med.*, 315:1241–1245 (1986).

P. Hartvig, H. Askmark, S. M. Aquilonius, L. Wiklund, and B. Lindstrom, "Clinical pharmacokinetics of intravenous and oral 9–amino–1,2,3,4–tetrahydroacridine, tacrine". *Eur. J. Clin. Pharmacol.*, 38:259–263 (1990).

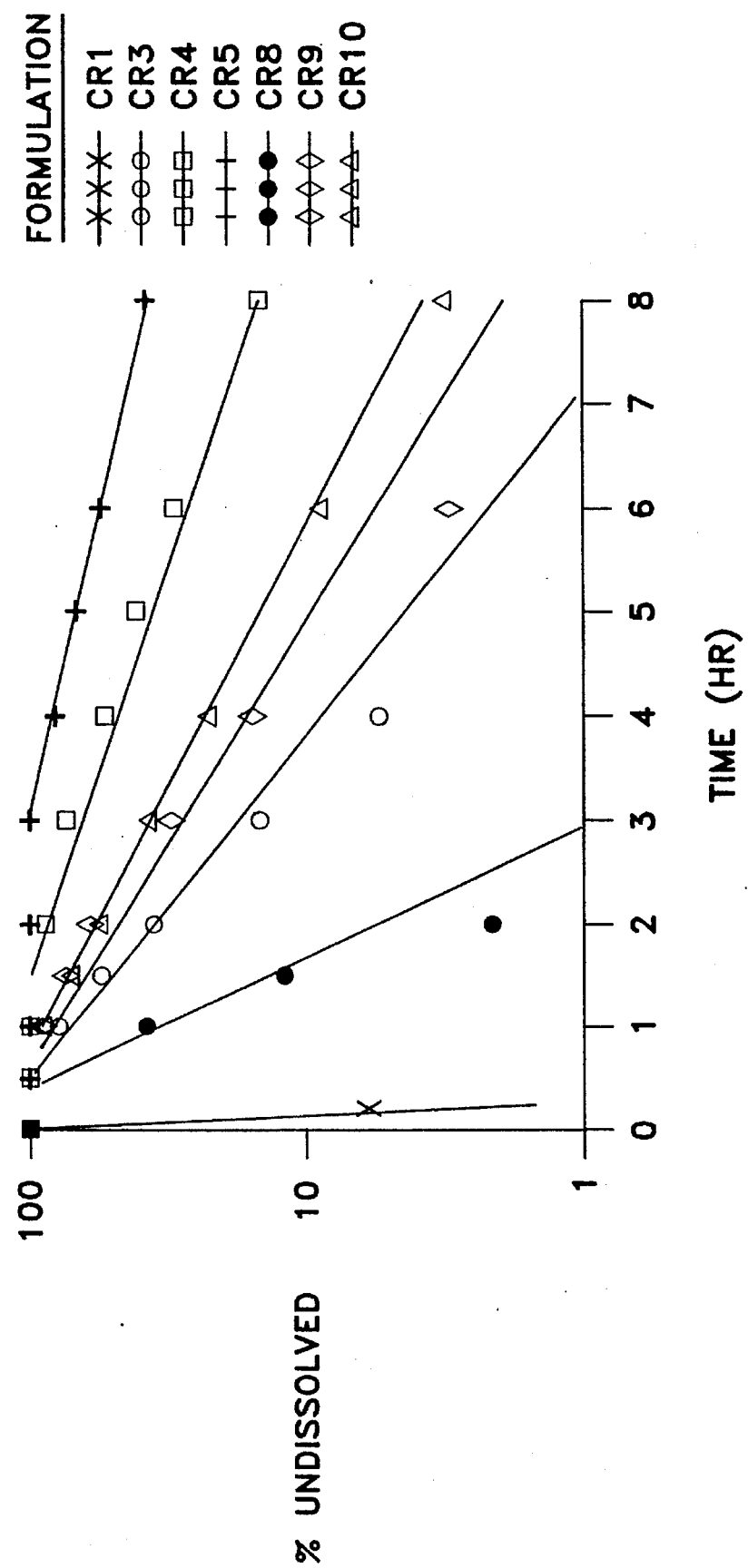

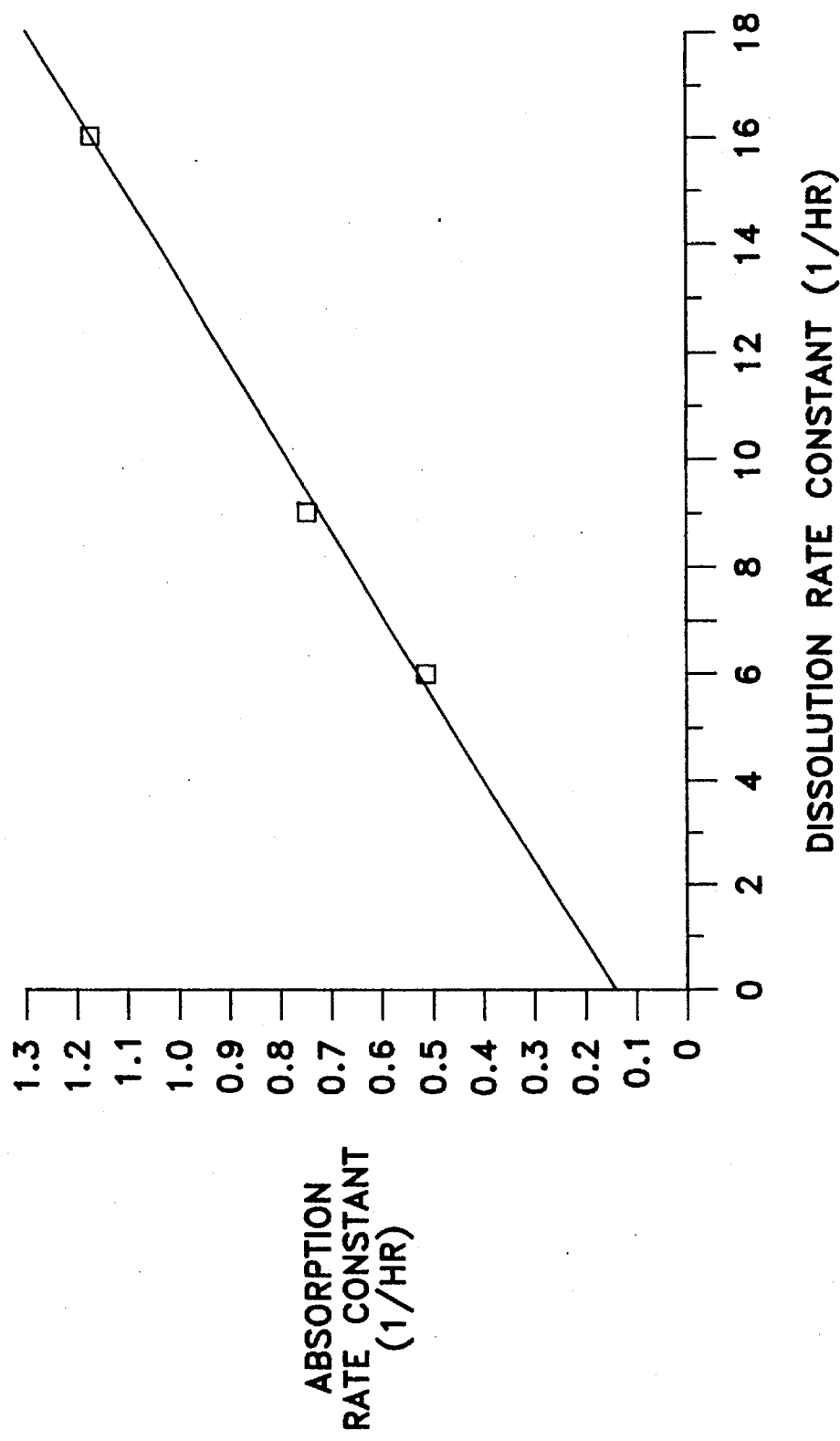

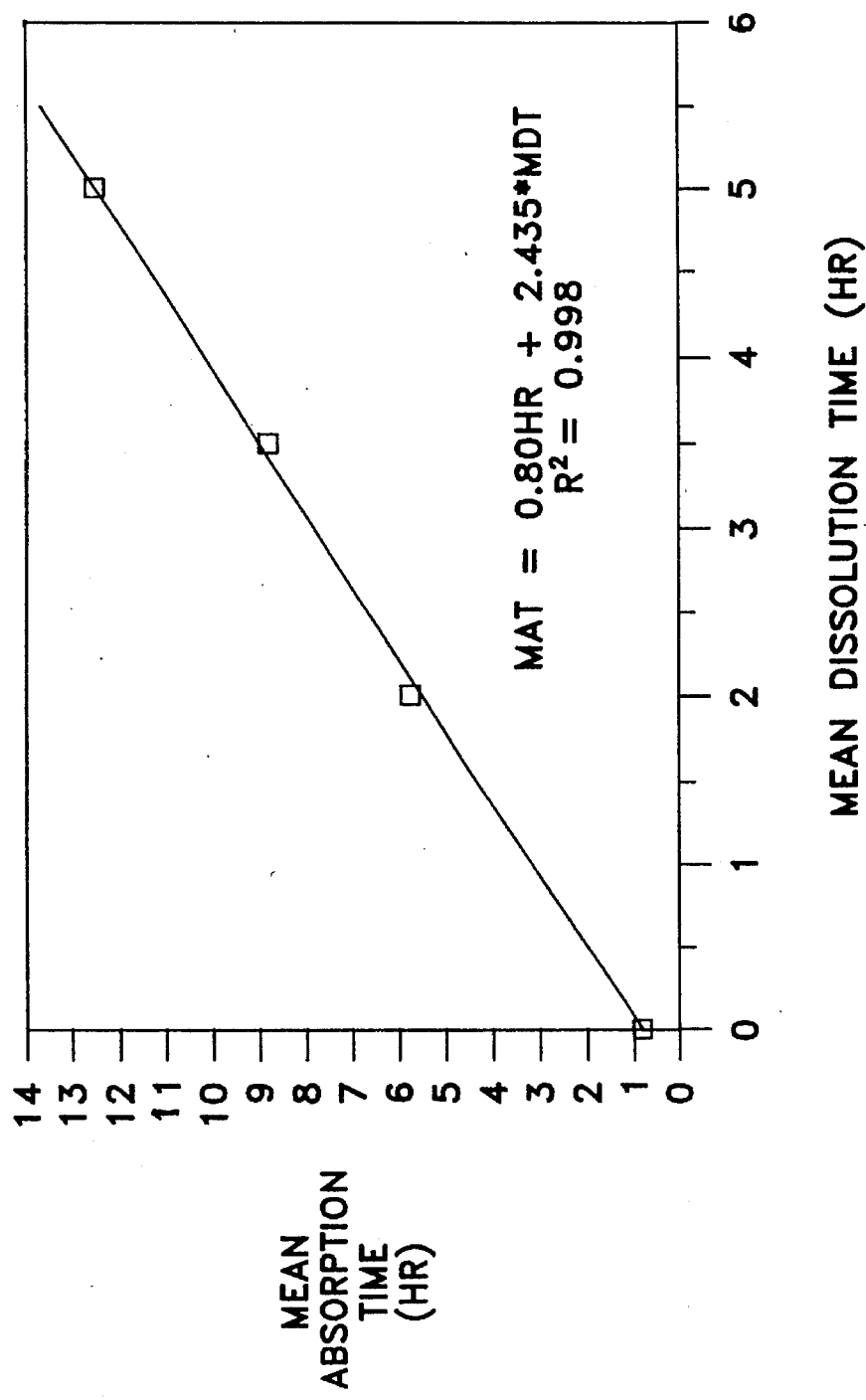

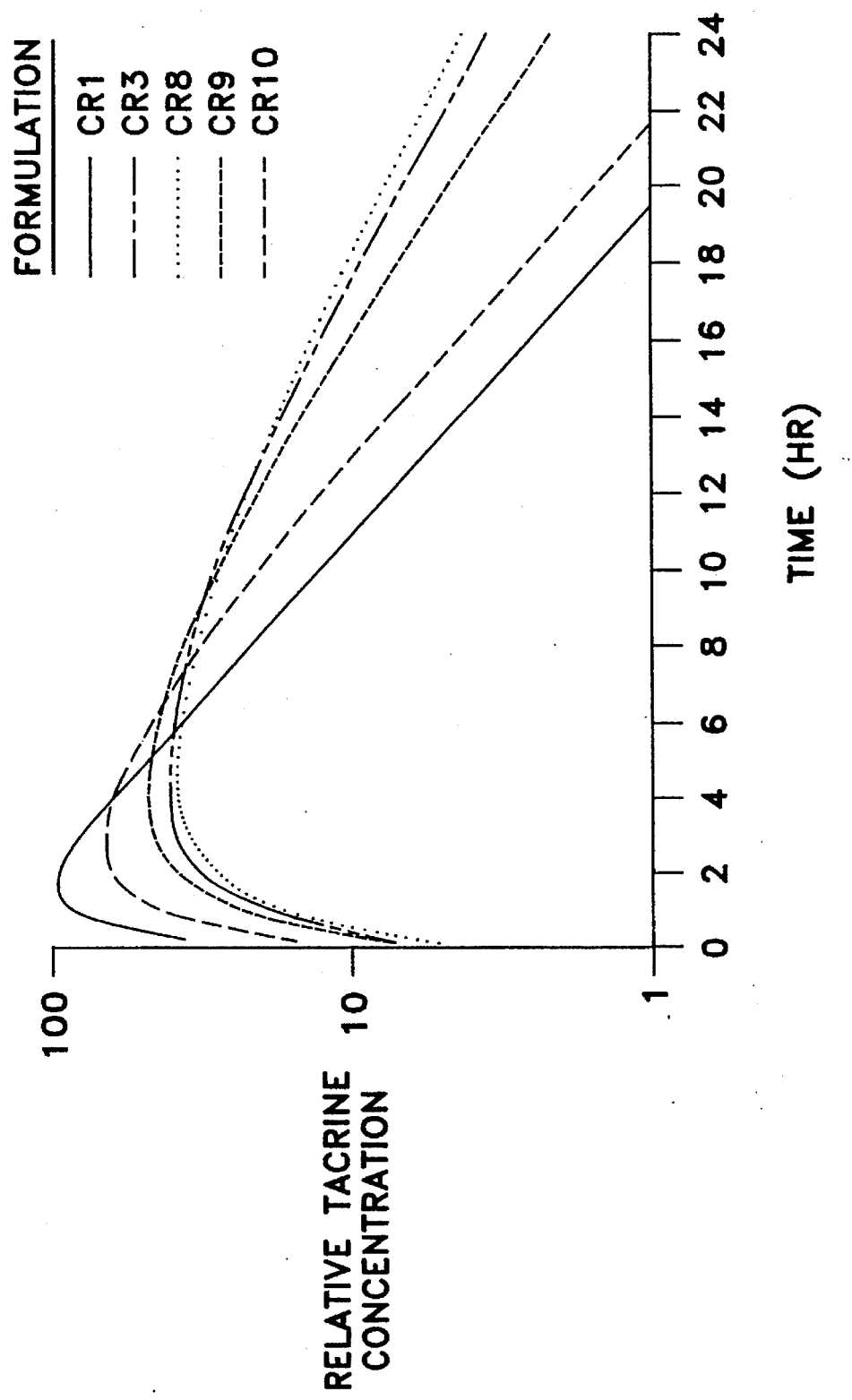

CONTROLLED RELEASE TACRINE DRUG DELIVERY SYSTEMS AND METHODS FOR PREPARING SAME

This is a continuation of application Ser. No. 08/096,140, abandoned, filed on Jul. 22, 1993.

BACKGROUND OF THE INVENTION

1. Field of the Invention

This invention pertains to controlled release tacrine drug delivery systems. The novel drug delivery systems contain an immediate release composition and a sustained release composition. Therapeutically effective amounts of the drug delivery systems may be utilized in a wide variety of pharmaceutically acceptable carriers to prepare medicated controlled release compositions. This invention also relates to methods for preparing and using these drug delivery systems and the medicated controlled release compositions in which they may be employed.

2. Description of the Background

Tacrine (1,2,3,4-tetrahydro-9-acridinamine hydrochloride) is a reversible cholinesterase inhibitor used as a respiratory stimulant in clinical anesthesiology for the reversal of postoperative sedation and prolongation of the muscle relaxation effect of succinylcholine. Tacrine has recently been shown to be a cognition activator and to improve some symptoms in Alzheimer's patients. Absorption and elimination half-life studies on tacrine have shown that the drug is rapidly absorbed and eliminated and that frequent administration is required to maintain therapeutic blood levels. Because treatment of Alzheimer's disease is long term, frequent administration of tacrine can be inconvenient and wide swings in blood levels may cause adverse effects. Hence, controlled-release forms of tacrine which release the drug uniformly over an extended period of time are more advantageous than conventional dosage forms.

Sustained release compositions for the sequential or timed release of medicaments are well known in the art. Generally such compositions contain medicament particles, normally administered in divided doses two or more times daily, mixed with or covered by a coating material which is resistant to degradation or disintegration in the stomach and/or in the intestine for a selected period of time. Release of the medicament may occur by leaching, erosion, rupture, diffusion or similar actions, depending upon the nature and thickness of the coating material.

A frequently encountered problem in the field of sustained release compositions is that many water-miscible drugs have a tendency to be dumped or surged into the body during the first hour or two after an oral dosage form is ingested. This problem is particularly acute when the sustained release compositions are administered with food.

U.S. Pat. No. 4,728,512, issued to Mehta et al., discloses a therapeutic composition containing three types of spheroids containing a medicament. The first type of spheroids are uncoated and provide an immediate release form, the second type of spheroids are coated with a pH sensititve material such as copolymers of methacrylic acid and methacrylic acid methyl ester or polyvinyl acetate phthalate, and the third type of spheroids are coated with a pH independent material having an undercoating selected from the group consisting of hydroxypropyl methylcellulose and hydroxypropyl methylcellulose containing carboxymethylcellulose or sodium starch glycolate and an overcoating of a neutral polymer based on polymethacrylic acid esters.

While the above sustained release compositions provide some degree of improved sustained release activity, none of the above compositions are entirely satisfactory. The present invention provides improved controlled release tacrine drug delivery systems without the disadvantages characteristic of previously known products. The present invention also provides methods for preparing and using these improved controlled release drug delivery systems and the medicated sustained release compositions in which they may be employed.

SUMMARY OF THE INVENTION

The present invention pertains to controlled release tacrine drug delivery systems comprising an immediate release composition and a sustained release composition wherein:

(1) the immediate release composition comprises in percentages by weight of the immediate release composition:
  (A) immediate release pellets comprising:
    (a) nonpareil seeds in an amount from about 25% to about 75%;
    (b) tacrine in an amount from about 10% to about 80%; and
    (c) a binding agent in an amount from about 1% to about 10%; and
  (B) a sealing layer over the immediate release pellets comprising:
    (a) a sealing agent in an amount up to about 6%, and
    (b) a first plasticizing agent in an amount up to about 5%; and (2) the sustained release composition comprises in percentages by weight of the sustained release composition;
  (A) the immediate release composition; and
  (B) a sustaining layer over the immediate release composition comprising;
    (a) a water-insoluble polymer in an amount from about 40% to about 90%;
    (b) a water-soluble polymer in an amount up to about 10%; and
    (c) a second plasticizing agent in an amount up to about 10%;

wherein the sustaining layer and the immediate release composition are present in the sustained release composition in a ratio by weight from about 1:9 to about 4:6, respectively, and the immediate release composition and the sustained release composition are present in the drug delivery system in a ratio by weight from about 0.01:1 to about 1:1, respectively. This invention also relates to methods for preparing these drug delivery systems and the medicated controlled release compositions in which they may be used.

BRIEF DESCRIPTION OF THE FIGURES

FIG. 9 is a graph showing the mean absorption time versus mean dissolution time for tacrine formulations (CR1, CR3, CR4, and CR5).

DETAILED DESCRIPTION OF THE INVENTION

Figure 1:
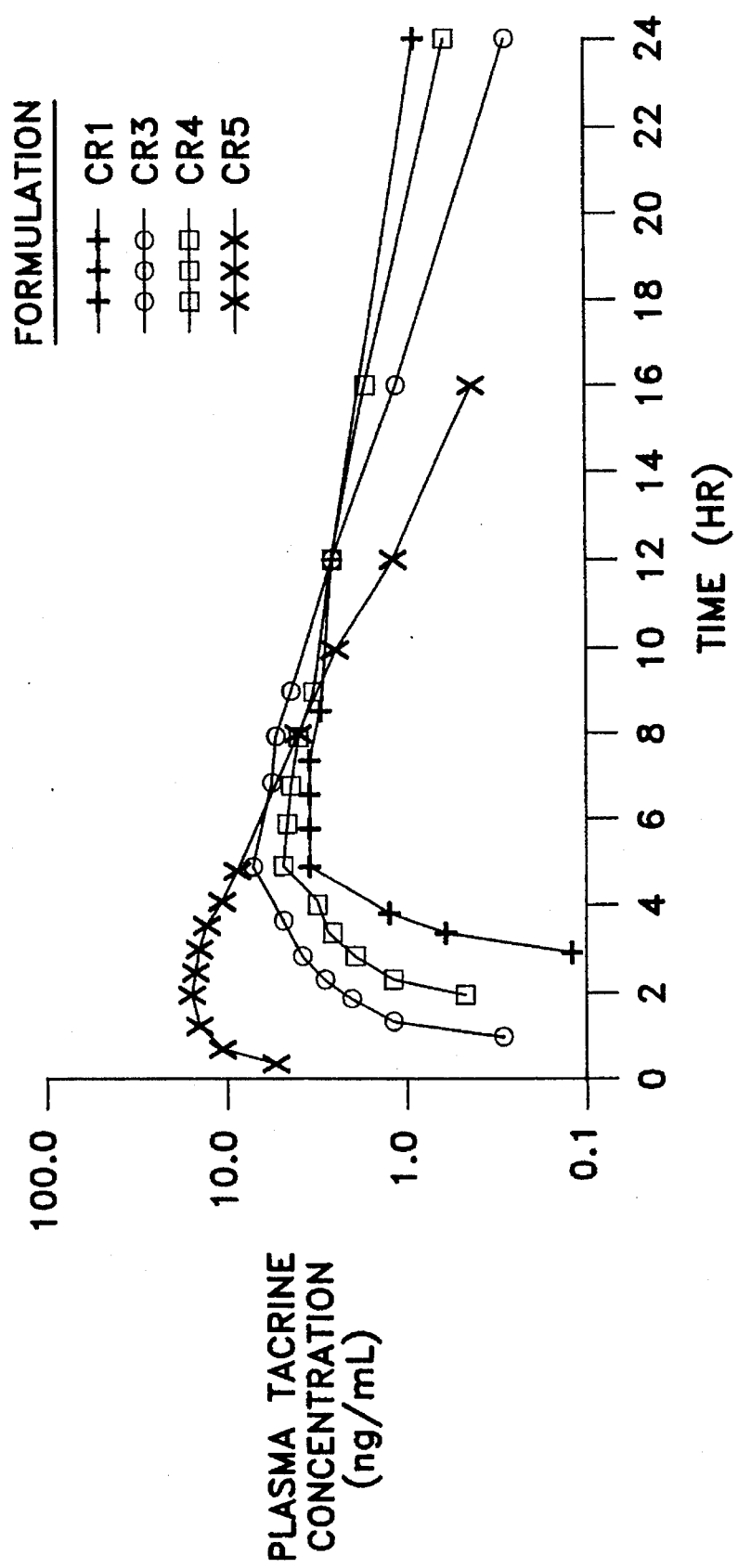
FIG. 1 is a graph showing the mean plasma tacrine concentrations following administration of single 40mg doses of tacrine CR capsules (CR1, CR3, CR4, and CR5) to healthy elderly volunteers. Top: semi-logarithmic scale; Bottom: linear scale.
Figure 1A:
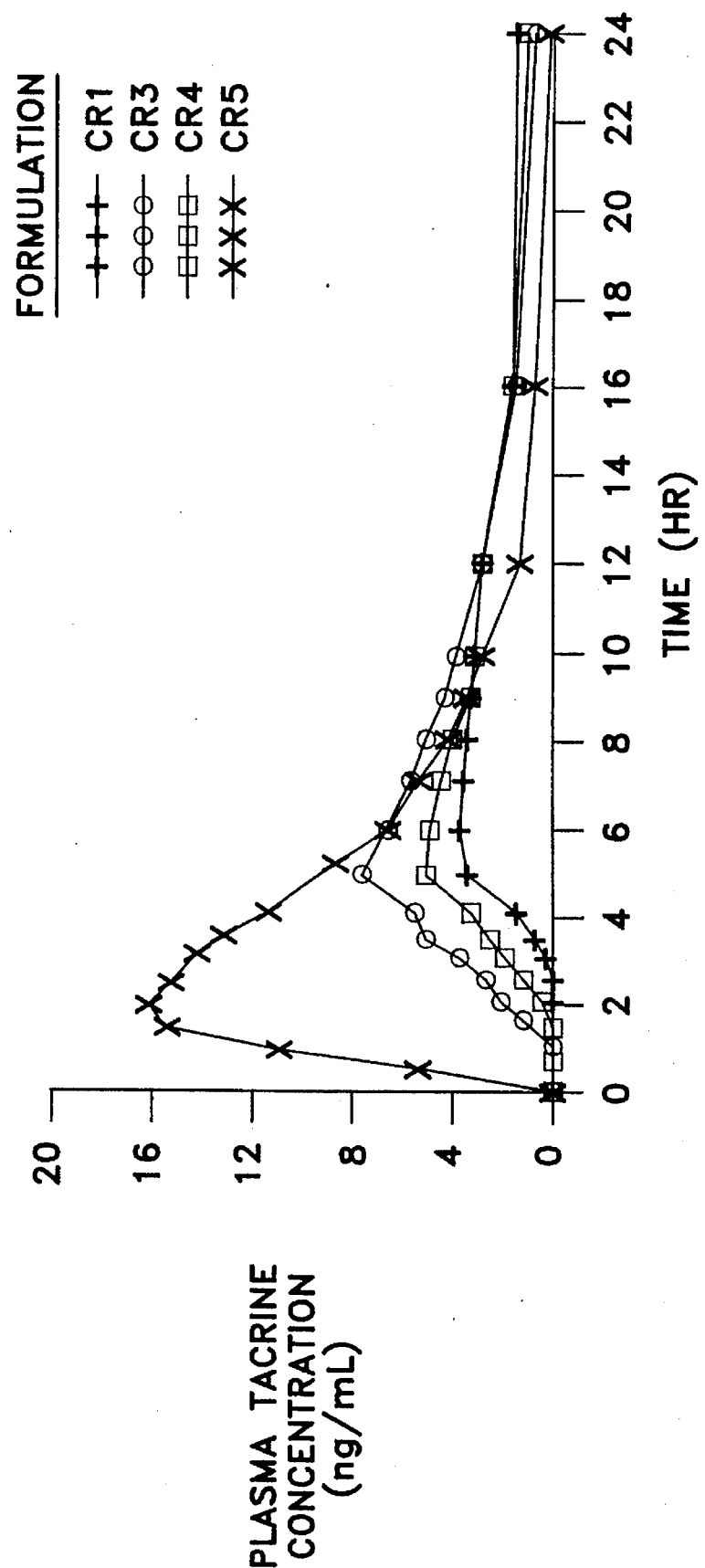
Figure 2:
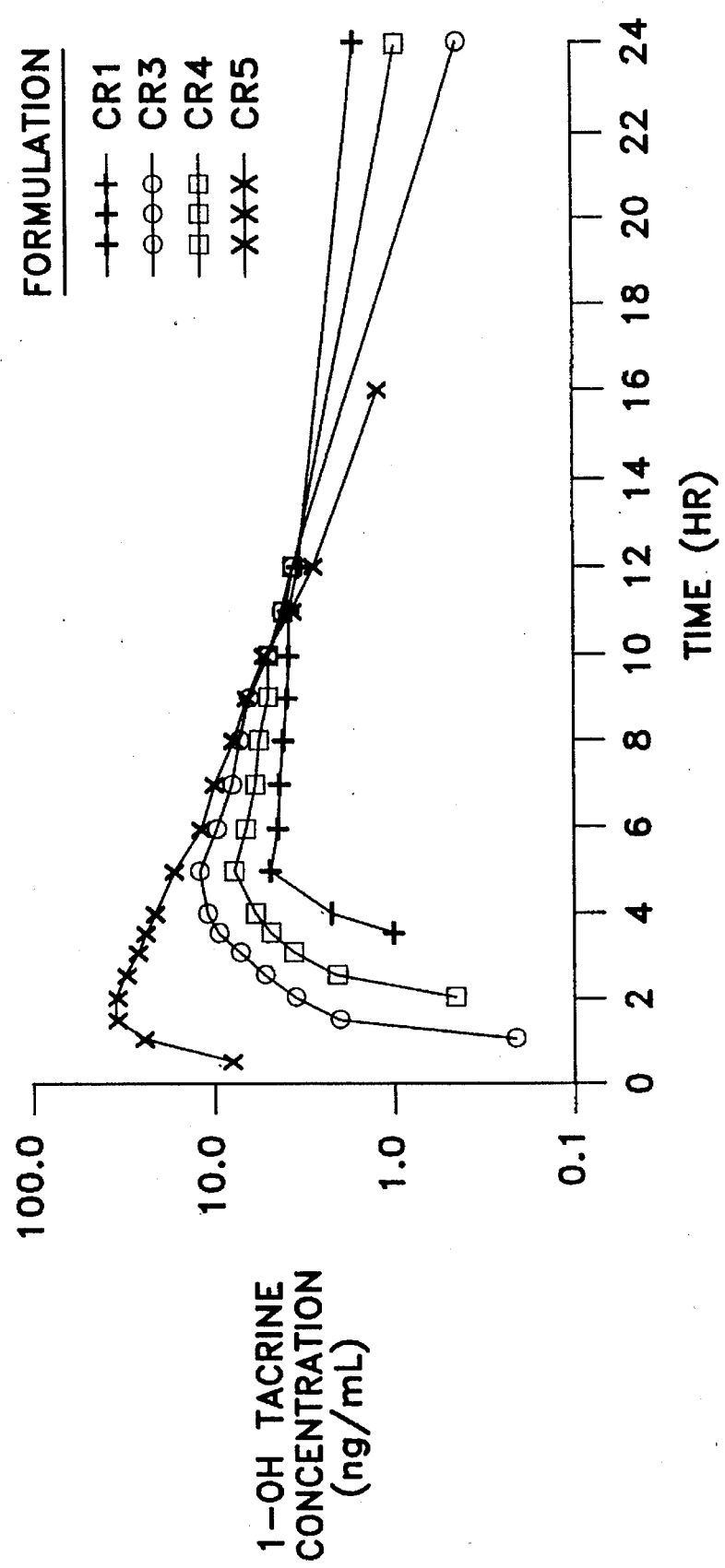
FIG. 2 is a graph showing the mean plasma 1-OH tacrine concentrations following administration of single 40 mg doses of tacrine CR capsules (CR1, CR3, CR4, and CR5) to healthy elderly volunteers. Top: semi-logarithmic scale; Bottom: linear scale.
Figure 2A:
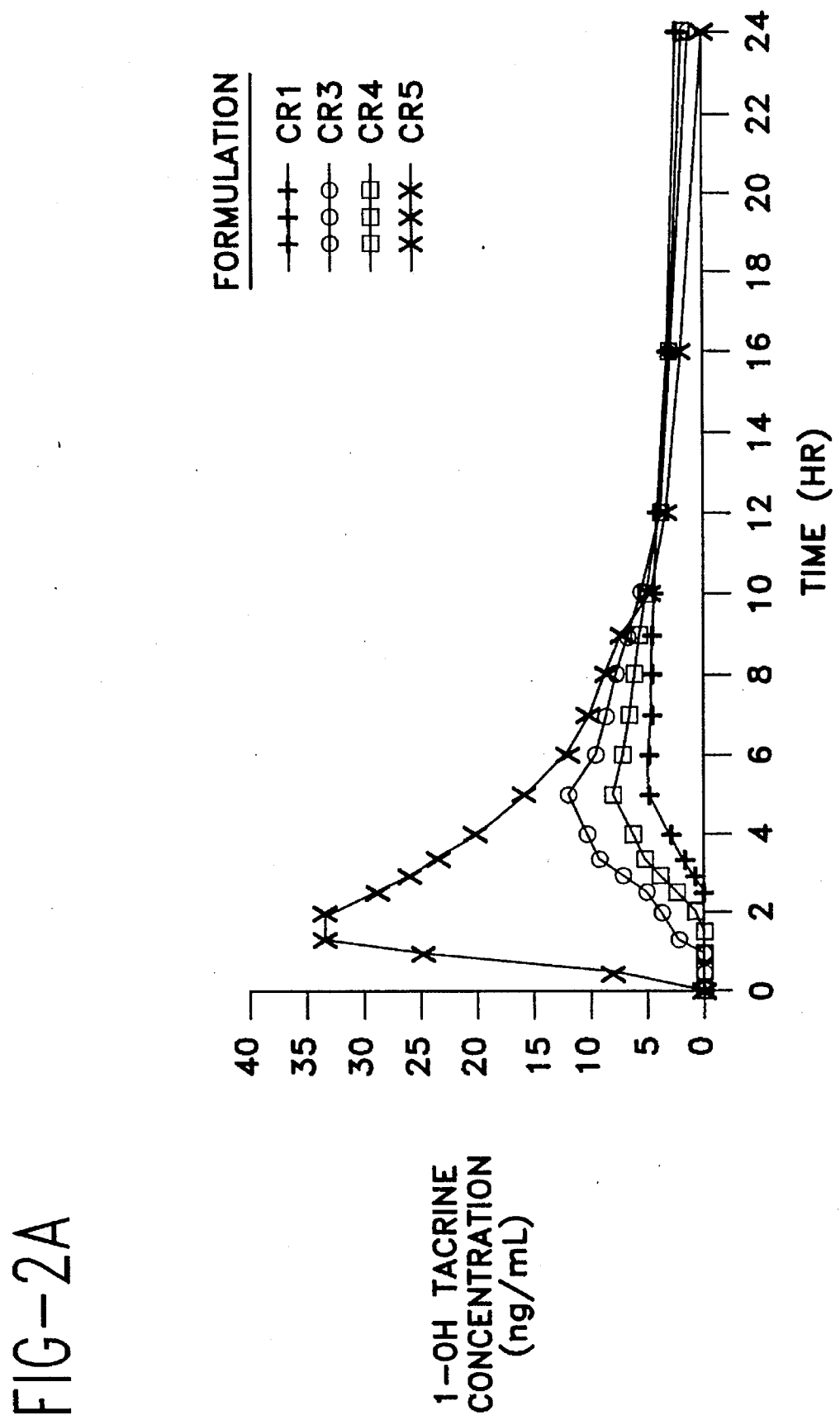

The present invention pertains to controlled release tacrine drug delivery systems having an immediate release composition and a sustained release composition. The immediate release composition consists of immediate release pellets containing nonpareil seeds, tacrine, and a binding agent, and a sealing layer covering the pellets. The sustained release composition consists of the immediate release composition coated by a sustaining layer. The sustaining layer comprises a water-insoluble polymer, a water-soluble polymer, and a plasticizer. The water-insoluble polymer provides a diffusion barrier for tacrine and controls its release rate and the water-soluble polymer increases the permeability of the sustaining coat. Applicants have discovered that by carefully controlling the ratio of water-soluble polymer to water-insoluble polymer in the sustained release composition, the release characteristics of tacrine capsules can be optimized. The tacrine delivery systems may be utilized in the form of pharmaceutical capsules or with a wide variety of pharmaceutically acceptable carriers to prepare medicated controlled release compositions. This invention also relates to methods for preparing and using these controlled release tacrine delivery systems and the medicated controlled release compositions in which they may be employed.

In accord with the present invention, the controlled release tacrine drug delivery systems contain an immediate release composition and a sustained release composition. The immediate release composition consists of immediate release pellets covered by a sealing layer. The immediate release pellets comprise nonpareil seeds, tacrine, and a binding agent. In general, the nonpareil seeds may be present in an amount from about 25% to about 75%.

Tacrine (1,2,3,4-tetrahydro-9-acridinamine hydrochloride) has recently been shown to be a cognition activator and to improve some symptoms in Alzheimer's patients. Tacrine may be used in many distinct physical forms well known in the pharmaceutical art to provide an initial dosage of the medicament and/or a further time-release form of the medicament. Without being limited thereto, such physical forms include free forms and encapsulated forms, and mixtures thereof.

The amount of tacrine used in the present invention may vary depending upon the therapeutic dosage recommended or permitted. In general, the amount of tacrine present is the ordinary dosage required to obtain the desired result. Such dosages are known to the skilled practitioner in the medical arts and are not a part of the present invention. In a preferred embodiment, tacrine is present in the immediate release composition in an mount from about 10% to about 80%, preferably from about 15% to about 60%, and more preferably from about 20% to about 50%, by weight of the immediate release composition.

Binding agents (binders) are compounds which exert a strong physiochemical attractive force between molecules. Suitable binding agents in the present invention include polyvinylpyrrolidone, acacia, gelatin, glucose, guar gum, pregelatinized starch, and sodium alginate, and cellulose derivatives such as ethylcellulose, hydroxypropyl cellulose, hydroxypropyl methylcellulose, methylcellulose, sodium carboxymethylcellulose, and the like, and mixtures thereof. Preferably, the binding agent is polyvinylpyrrolidone.

Povidone (USP/NF, 1-ethenyl-2-pyrrolidone polymers, polyvinylpyrrolidone, PVP) is a free flowing amorphous powder soluble in water and organic solvents. Povidine is a synthetic polymer consisting of linear 1-vinyl-2-pyrrolidone groups. The degree of polymerization results in polymers of various molecular weights ranging from about 10,000 to about 700,000. Povidine may be represented by the formula:

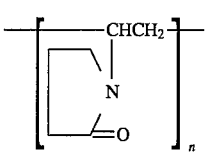

The amount of binding agent in the immediate release pellets is an effective amount to prepare immediate release pellets. An effective amount of binding agent is an amount which will bind tacrine to the nonpareil seeds and thereby provide an immediate release composition. The amount of binding agent is a matter of preference, subject to such factors as the type of nonpareil seeds employed, the exact type and amount of povidone employed, and the other ingredients in the drug delivery system. Thus, the amount of binding agent may be varied in order to obtain the result desired in the final product. In general, the binding agent will be present in an amount from about 1% to about 10%, and preferably from about 2% to about 8%, and more preferably from about 2% to about 5%, by weight of the immediate release composition.

In a preferred embodiment, the immediate release composition further comprises an anti-adhering agent. Anti-adhering agents (anti-adherents, dispersing gents) are surface-active agents which may be added to a suspension to promote uniform separation of extremely fine (colloidal) solid particles. Suitable anti-adhering agents in the present invention include polymeric electrolytes, condensed silicates, polyphosphates, lignin derivatives including aluminum stearate, aluminum laurate, magnesium stearate, calcium stearate, zinc stearate, talc, kaolin, fumed silica, and the like, and mixtures thereof. Preferably, the anti-adhering agent is talc. The anti-adhering agent, when present in the immediate release composition, will be present in an amount up to about 20%, preferably from about 2% to about 15%, and more preferably from about 5% to about 10%, by weight of the immediate release composition.

As set out above, the immediate release pellets of the drug delivery system are covered by a sealing layer to improve flow, prevent drug loss by attrition, and reduce electrostatic charge during processing. The sealing layer comprises a sealing agent and a first plasticizing agent.

Suitable sealing agents (sealers) in the present invention include cellulose derivatives such as hydroxypropyl cellulose, hydroxypropyl methylcellulose, and the like, and mixtures thereof. Preferably, the sealing agent is hydroxypropyl methylcellulose. The sealing agent is present in an amount up to about 6%, preferably up to about 4%, and more preferably from about 0.5% to about 3%, by weight of the immediate release composition.

The sealing layer also comprises a first plasticizing agent. Plasticizing agents (plasticizers) are organic molecules added to polymers to facilitate processing by increasing the flexibility and toughness of the final product by internally modifying (solvating) the polymer molecule. Plasticizing agents should be soluble in the polymer they are designed to plasticize and should be safe for the intended use. Suitable first plasticizing agents in the present invention are nonvolatile organic liquids and low melting solids, such as esters of phthalic acid, adipic acid, and sebacic acid, and polyols such as ethylene glycol, polyethylene glycol, and their, derivatives, tricresyl phosphate, castor oil, and the like, and mixtures thereof. Other suitable partly water-soluble to water-insoluble first plasticizing agents that may be employed are dibutyl sebacate, triethyl citrate, tributyl citrate, triacetin, and acetylated mono-, di- and triglycerides, and the like, and mixtures thereof. Other suitable first plasticizing agents include acetyl triethyl citrate, triethyl citrate, acetyl tributyl citrate, tributyl titrate, and the like, and mixtures thereof. Preferably, the first plasticizing agent is polyethylene glycol. The first plasticizing agent is present in an amount up to about 5%, preferably up to about 4%, and more preferably from about 0.1% to about 1%, by weight of the immediate release composition.

In addition to the immediate release composition, the controlled release tacrine drug delivery systems of the present invention also include a sustained release composition. The sustained release composition consists of the immediate release composition covered by a sustaining layer. The sustaining layer comprises a water-insoluble polymer, a water-soluble polymer, and a second plasticizing agent.

The water-insoluble polymers useful in the sustaining layer are film forming polymers, which are preferably available as aqueous colloidal dispersions containing spherical, solid or semisolid particles less than about one (1) micron in diameter, and typically less than about 0.1 micron in diameter. Aqueous colloidal mixtures are generally very fluid at concentrations from about 20% to about 40%. Suitable film forming polymers in the present invention include cellulose derivatives such as ethylcellulose, and the like, and mixtures thereof. Other suitable film forming polymers in the present invention include aqueous acrylic resin dispersions such as polyacrylamide, polyacryldextran, polyalkyl cyanoacrylate, polymethyl methacrylate, and the like, and mixtures thereof. In a preferred embodiment, the film forming polymer is a cellulose derivative such as ethylcellulose. In a more preferred embodiment, the film forming polymer is the commercially available aqueous polymeric dispersion manufactured under the tradename AQUACOAT (24.5%–30% ethyl cellulose), by FMC Corporation, Princeton, N.J. In another more preferred embodiment, the film forming polymer is the commercially available aqueous polymeric dispersion manufactured under the tradename SURELEASE (containing 24.5%–29.5% ethyl cellulose, dibutyl sebacate and oleic acid as plasticizing agents, and fumed silica as an antiadherent), by Colorcon, Inc., West Point, Penn.

Other water-insoluble polymers useful in the sustaining layer are pH-independent water-insoluble polymers such as acrylic polymers. Suitable water-insoluble polymers include aqueous acrylic resin dispersions such as polyacrylamide, polyacryldextran, polyalkyl cyanoacrylate, polymethyl methacrylate, methacrylic resin copolymer, and the like, and mixtures thereof. Preferred resins are the Eudragits™ (methacrylic resin copolymer), made by Rohm Pharma. Eudragit NE30D™ is highly preferred.

The amount of water-insoluble polymer in the sustained release composition is an effective amount to prepare a sustaining layer. An effective amount of a water-insoluble polymer is an amount which will provide a satisfactory diffusion barrier for tacrine and thereby control its release rate. The amount of water-insoluble polymer is a matter of preference, subject to such factors as the type of water-insoluble polymer employed, the exact type and amount of water-soluble polymer employed, and the other ingredients in the drug delivery system. Thus, the amount of water-insoluble polymer may be varied in order to obtain the result desired in the final product. In general, the water-insoluble polymer will be present in an amount from about 40% to about 90%, preferably from about 45% to about 85%, and more preferably from about 50% to about 80%, by weight of the sustained release composition.

The water-soluble polymers useful in the sustaining layer include cellulose derivatives such as hydroxypropyl cellulose, hydroxypropyl methylcellulose, sodium carboxymethylcellulose, and the like, and mixtures thereof. In a preferred embodiment, the film forming polymer is hydroxypropyl methylcellulose.

The amount of water-soluble polymer in the sustained release composition is an effective amount to prepare a sustaining layer. An effective amount of a water-soluble polymer is an amount which will increase the permeability of the sustaining coat and thereby control its release rate. The amount of water-soluble polymer is a matter of preference, subject to such factors as the type of water-soluble polymer employed, the exact type and amount of water-insoluble polymer employed, and the other ingredients in the drug delivery system. Thus, the amount of water-soluble polymer may be varied in order to obtain the result desired in the final product. In general, the water-soluble polymer will be present in an amount up to about 10%, preferably up to about 5%, and more preferably from about 0.5% to about 1.5%, by weight of the sustained release composition.

The sustaining layer also comprises a second plasticizing agent. Suitable second plasticizing agents in the present invention are nonvolatile organic liquids and low melting solids, such as esters of phthalic acid, adipic acid, and sebacic acid, and polyols such as ethylene glycol, polyethylene glycol, and their, derivatives, tricresyl phosphate, castor oil, and the like, and mixtures thereof. Other suitable partly water-soluble to water-insoluble second plasticizing agents that may be employed are dibutyl sebacate, triethyl titrate, tributyl citrate, triacetin, and acetylated mono-, di- and triglycerides, and the like, and mixtures thereof. Other suitable second plasticizing agents include acetyl triethyl citrate, triethyl citrate, acetyl tributyl citrate, tributyl titrate, and the like, and mixtures thereof. Preferably, the second plasticizing agent is triethyl citrate. The second plasticizing agent is present in an amount up to about 10%, preferably from about 1% to about 6%, and more preferably from about 1% to about 5%, by weight of the sustained release composition.

The immediate release composition and sustained release composition in the controlled release tacrine drug delivery systems of the present invention may also contain conventional excipients and additives which function to facilitate processing or storage. Thus antifoam agents, fillers, plasticizing agents, coloring agents, flavoring agents, perfumes, sweetening agents, surface active agents, lubricants, stabilizing agents, anti-tacking agents, and the like, and mixtures thereof, may be employed.

The weight ratio of sustaining layer to immediate release composition in the sustained release composition is the ratio containing sufficient sustaining layer to prevent potential premature release of the medicament from the immediate release composition without forming a composition so large as to be therapeutically unsuitable for use. In general, the weight ratio of sustaining layer to immediate release composition in the sustained release composition is from about 1:9 to about 4:6, preferably from about 1:9 to about 3:7, and more preferably from about 1:9 to about 2:8, respectively.

The weight ratio of immediate release composition to sustained release composition in the controlled release tacrine drug delivery system is the ratio containing sufficient sustained release composition to release the drug uniformly over an extended period of time. In general, the weight ratio of immediate release composition to sustained release composition in the drug delivery system is from about 0.01:1 to about 1:1, preferably from about 1:9 to about 2:8, and more preferably from about 2:8 to about 4:6, respectively.

The present invention is also directed at methods for preparing the controlled release tacrine delivery systems. In general, the drug delivery systems are prepared by forming core pellets containing tacrine hydrochloride monohydrate using fluid-bed tangential coating equipment. The core pellets are subsequently coated with the components of the sustaining layer to impart various controlled release profiles. By combining immediate release pellets with sustained release pellets or extended release pellets in the same capsule to provide an initial loading dose, additional controlled release dissolution profiles may be obtained. Pellets of each of these formulations may be developed to fill size 2 hard gelatin capsules to provide 40 mg of tacrine base per capsule.

The drug delivery systems of the present invention may be prepared using standard techniques and equipment known to those skilled in the art. The core pellets may be prepared by suspension layering, powder layering, or extrusion/spheronization techinques, or other standard procedures, using standard techniques and equipment known to those skilled in the art. The core pellets may be coated by fluid-bed tangential coating, pan coating, or other standard coating procedures using standard techniques and equipment known to those skilled in the art. The exact conditions for forming and coating pellets will vary with the particular apparatus selected and are readily determined by those skilled in the art without the need for undue experimentation. Fluid-bed tangential coating and pan coating are well known in the arts and therefore the selection of the specific apparatus will be apparent to the artisan.

In a specific embodiment, the present invention is directed at a method for preparing a controlled release tacrine drug delivery system comprising an immediate release composition and a sustained release composition, which comprises the steps of:

(i) providing the following ingredients:
  (1) the immediate release composition comprises in percentages by weight of the immediate release composition:
    (A) immediate release pellets comprising:
      (a) nonpareil seeds in an amount from about 25% to about 75%;
      (b) tacrine in an amount from about 10% to about 80%; and
      (c) a binding agent in an amount from about 1% to about 10%; and
    (B) a sealing layer over the immediate release pellets comprising:
      (a) a sealing agent in an amount up to about 6%, and
      (b) a first plasticizing agent in an amount up to about 5%; and
  (2) the sustained release composition comprises in percentages by weight of the sustained release composition;
    (A) the immediate release composition; and
    (B) a sustaining layer over the immediate release composition comprising;
      (a) a water-insoluble polymer in an mount from about 40% to about 90%;
      (b) a water-soluble polymer in an amount up to about 10%;
and
      (c) a second plasticizing agent in an amount up to about 10%;
wherein the sustaining layer and the immediate release composition are present in the sustained release composition in a ratio by weight from about 1:9 to about 4:6, respectively, and the immediate release composition and the sustained release composition are present in the drug delivery system in a milo by weight from about 0.01:1 to about 1:1, respectively;

(ii) forming an aqueous suspension of the tacrine and the binding agent from step (i)(1)(A) and layering the suspension on the nonpareil seeds to form immediate release pellets;

(iii) forming an aqueous mixture of the sealing agent and first plasticizing agent from step (i)(1)(B) and coating the immediate release pellets to form the immediate release composition;

(iv) forming an aqueous dispersion of the water-insoluble polymer, water-soluble polymer, and second plasticizing agent from step (i)(2)(B) and coating a portion of the immediate release composition to form the sustained release composition; and (v) admixing the immediate release composition and the sustained release composition in a ratio by weight from about 0.01:1 to about 1:1, respectively, to form the controlled release tacrine drug delivery system.

Once prepared, the controlled release latrine drug delivery systems may be stored for future use or may be formulated with conventional additives such as pharmaceutically acceptable carders to prepare a wide variety of medicated controlled release compositions to suit particular applications.

The novel medicated controlled release compositions may also be in the form of a pharmaceutical suspension. Pharmaceutical suspensions of this invention may be prepared by conventional methods long established in the art of pharmaceutical compounding. Suspensions may contain adjunct materials employed in formulating the suspensions of the art. The suspensions of the present invention can comprise:

(a) preservatives such as benzoic acid, sorbic acid, methyl paraben, and propyl paraben. Preservatives are generally present in mounts up to about 1%, and preferably from about 0.05% to about 0.5%, by weight of the suspension;

(b) buffers such as citric acid-sodium citrate, phosphoric acid-sodium phosphate, and acetic acid-sodium acetate which may be present in amounts up to about 1%, and preferably from about 0.05% to about 0.5%, by weight of the suspension;

(c) suspending agents or thickeners such as cellulosics like methylcellulose, carrageenans like alginic acid and its derivatives, xanthan gums, gelatin, acacis, and microcrystalline cellulose which may be present in amounts up to about 20%, and preferably from about 1% to about 15%, by weight of the suspension;

(d) antifoaming agents such as dimethyl polysiloxane which may be present in amounts up to about 0.2%, and preferably from about 0.01% to about 0.1%, by weight of the suspension;

(e) sweetening agents such as those sweeteners well known in the art, including both natural and artificial sweeteners. Sweetening agents such as monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, glycyrrhizin, and sugar alcohols such as sorbitol, mannitol, maltitol, hydrogenated starch hydrolysates and mixtures thereof may be utilized in amounts up to about 60%, and preferably from about 20% to about 50%, by weight of the suspension. Water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin, and the like may be utilized in amounts from about 0.001% to about 5%, by weight of the suspension;

(f) flavoring agents such as those flavors well known to the skilled artisan, such as natural and artificial flavors and mints, such as peppermint, menthol, citrus flavors such as orange and lemon, artificial vanilla, cinnamon, various fruit flavors, both individual and mixed and the like may be utilized in amounts from about 0.5% to about 5%, by weight of the suspension;

(g) coloring agents such as pigments which may be incorporated in amounts up to about 6%, by weight of the suspension. A preferred pigment, titanium dioxide, may be incorporated in amounts up to about 2%, and preferably less than about 1%, by weight of the suspension. The coloring agents may also include natural food colors and dyes suitable for food, drug and cosmetic applications. These coloring agents are known as F.D.& C. dyes and lakes. The materials acceptable for the foregoing uses are preferably water-soluble. Such dyes are generally present in amounts up to about 0.25%, and preferably from about 0.05% to about 0.2%, by weight of the suspension;

(h) decolorizing agents such as sodium metabisulfite, ascorbic acid and the like may be incorporated into the suspension to prevent color changes due to aging. In general, decolorizing agents may be used in amounts up to about 0.25%, and preferably from about 0.05% to about 0.2%, by weight of the suspension; and (i) vehicles such as propylene glycol, polyethylene glycol, edible oils such as animal, vegetable and mineral oils, and the like may be used to solubilize the flavoring agents. In general, vehicles may be used in amounts up to about 10%, and preferably from about 2% to about 5%, by weight of the suspension.

The pharmaceutical suspensions of the present invention may be prepared as follows:

(A) admix the thickener with the vehicle heated to a temperature from about 40° C. to about 95° C., preferably from about 40° C. to about 70° C., to form a dispersion if the thickener is soluble in the vehicle or a solution if the thickener is soluble in the soluble;

(B) admix the sweetening agent with the vehicle to form a solution;

(C) admix the controlled release composition with the thickener-vehicle admixture to form a uniform thickener-controlled release composition;

(D) combine the sweetener solution with the thickener-controlled release composition and mix until uniform; and (E) admix the optional adjunct materials such as coloring agents, flavoring agents, decolorants, solubilizing agents, antifoaming agents, buffers and additional vehicle with the mixture of step (D) to form the suspension.

To achieve acceptable stability and quality as well as good taste and mouth feel in a controlled release formulation several considerations are important. These considerations include the amount of active substance per tablet, the flavoring agent employed, the degree of compressibility of the tablet and the organoleptic properties of the pharmaceutical composition.

Throughout this application, various publications have been referenced. The disclosures in these publications are incorporated herein by reference in order to more fully describe the state of the art.

The present invention is further illustrated by the following examples which are not intended to limit the effective scope of the claims. All parts and percentages in the examples and throughout the specification and claims are by weight of the final composition unless otherwise specified.

EXAMPLES 1–7

The following examples were carried out to develop controlled release pellet formulations for tacrine hydrochloride monohydrate that reduce the dosing frequency to improve convenience and patient compliance. Core pellets containing tacrine hydrochloride monohydrate were manufactured using fluid-bed tangential coating equipment. Core pellets subsequently were coated with different types of polymers that impart various controlled release profiles. A water-soluble polymer coat (hydroxypropyl methylcellulose 2910) provides pellets with an immediate release (IR) dissolution profile. A water-insoluble polymer coat (ethylcellulose aqueous dispersion) provides pellets with sustained release (SR) characteristics where the release rate can be controlled by the thickness of the coat and the formulation of the coating preparation. An acid-insoluble but alkaline-soluble polymer coat (Eudragit L30D, a copolymer of polymethacrylic acid and acrylic acid ester) provides pellets with pH-dependent enteric release (ER) profiles. These coated pellets are referred to as IR, SR, and ER Pellets, respectively. By combining IR pellets with SR and/or ER pellets in the same capsule to provide an initial loading dose, additional controlled release dissolution profiles are obtained. Pellets of each of these formulations were developed to be properly filled into size 2 hard gelatin capsules to provide 40 mg of tacrine base per capsule.

The following table describes the product references made throughout this section.

| Formulation | Dissolution Profile of Pellets in Formulation |
|---|---|
| CR1 (37) | Immediate Release (IR) |
| CR2 (38) | Enteric Release (ER) |
| CR3 (39) | Sustained Release (SR1) |
| CR4 (40) | Sustained Release (SR2) |
| CR5 (41) | Sustained Release (SR3) |
| CR6 (42) | Immediate and Enteric Release (IR + ER) |
| CR7 (43) | Immediate and Sustained Release (IR + SR3) |

Collectively these products are referred as control release capsules.

Core pellets

The core pellets were manufactured by the suspension-layering method using fluid-bed tangential coating equipment. This process is dust-free, fast, and efficient. A suspension containing tacrine hydrochloride monohydrate (15% w/w), spray talc (7.5% w/w), and povidone (1.5% w/w) in water was applied to sugar spheres of 20–25 mesh to obtain core pellets with an approximate drug loading of 20%. Povidone was used as a binder and spray talc was used as an antiadherent to reduce tackiness during the layering process. The composition of the core pellets containing 40 mg of tacrine base is provided in Table 1.

TABLE 1

| Composition of Core Pellets per 40 mg Tacrine Base | |
|---|---|
| Ingredient | Quantity (mg) |
| Sugar Spheres NF, 20–25 mesh | 167.29 |
| Tacrine Hydrochloride Monohydrate | 51.02 |
| Povidone USP | 5.10 |
| Spray Talc | 25.51 |

CR1 Capsules (Formulation 37)

The IR pellets were prepared by coating the core pellets with a water-soluble polymer to improve flow and to eliminate electrostatic charges during processing. The coating preparation consisted of hydroxypropyl methylcellulose (HPMC) 2910 (6% w/w), polyethylene glycol (PEG) 3350 (15 w/w), spray talc (1% w/w), and water (92.0% w/w). The core pellets were coated to 2% weight increase using fluid-bed tangential coating equipment. Both the core pellets and IR pellets exhibited immediate release characteristics.

CR2 Capsules (Formulation 38)

The ER Pellets were manufactured by coating the pellets with Eudragit L3OD, an aqueous dispersion (30% w/w) containing a copolymer based on polymethacrylic acid and acrylic acid esters. This copolymer is insoluble below pH 5.5. Although the copolymer is soluble above pH 5.5, the dissolution rate is a function of the pH of the dissolution media. As the pH increases, the dissolution rate of this polymer increases so that at the pH of the current USP <724> dissolution media for enteric coated articles (pH 6.8), dissolution is rapid. The coating formulation consisted of Eudragit L30D (40% w/w), triethyl titrate (3% w/w), spray talc (0.75% w/w), and water (56.25% w/w). The core pellets were coated to 15.7% weight increase using fluid-bed tangential coating equipment.

CR3 Capsules (Formulation 39)

The SR1 Pellets (Formulation 39) were manufactured by coating the core pellets with an aqueous dispersion (30%w/w) containing a water-insoluble polymer, ethylcellulose, and a water-soluble polymer, hydroxypropyl methylcellulose. The coating formulation consisted of ethylcellulose aqueous dispersion (37.6% w/w), triethyl citrate (2.82% w/w), spray talc (0.15% w/w), hydroxypropyl methylcellulose 2910 (0.75% w/w), and water (58.68% w/w). The coating formulation was applied to the core pellets to 15% weight increase using fluid-bed tangential coating equipment. The coated pellets were subsequently overcoated with the same formulation as Formulation 37 to overcome stickiness. The finished pellets were cured by fluidization at 60° C. product temperature for 30 to 60 minutes in the coating equipment immediately following the sustained coating process in order to promote film coating coalescence.

CR4 Capsules (Formulation 40)

The SR2 Pellets (Formulation 40) were prepared in a similar manner as that described for Formulation 39. The SR coating formulation consisted of ethylcellulose aqueous dispersion (38.08% w/w), triethyl citrate (3.34% w/w), spray talc (0.15% w/w), and water (58.34% w/w). The SR coating formulation was applied to the core pellets to 15% weight increase. The ethylcellulose coated pellets were subsequently overcoated with the same overcoat formulation as previously described for Formulation 39 and cured similarly using the same equipment. A slower dissolution rate for Formulation 40 compared to Formulation 39 results from the absence of hydroxypropyl cellulose in the sustaining coat.

CR5 Capsules (Formulation 41)

The formulation of SR3 Pellets (Formulation 41) is very similar to that of Formulation 40. The same SR coating formulation and overcoat formulation as previously described for Formulation 40 was applied to the core pellets employing the same processing parameters and using the same equipment, except that the sustained release coating was applied to 25% weight increase. Because of the thicker sustained release coat, Formulation 41 exhibited the slowest dissolution rate among the three types of SR pellets.

CR6 Capsules (Formulation 42)

Pellets for Formulation 42 were prepared by blending the IR pellets (Formulation 37) and the ER pellets (Formulation 38) such that each portion provided 20 mg of tacrine base per capsule. Therefore, each CR6 Capsule contains a loading dose of 20 mg and a delayed dose of 20 mg.

CR7 Capsules (Formulation 43)

Pellets for Formulation 43 were prepared by blending the IR pellets (Formulation 37) and the SR3 Pellets (Formulation 41) such that each portion provided 20 mg of tacrine base per capsule. Therefore, each CR7 Capsule contains a loading dose of 20 mg and a delayed dose of 20 mg.

Quantitative Formula for the Capsule Products

Formulation No. 37
(Immediate Release (IR) Pellets in CR1 Capsule)
Label Claim: 40 mg (as base)

| | Amount/1000 Capsules |
|---|---|
| Core Pellets | |
| Tacrine Hydrochloride Monohydrate | 51.02 g |
| Sugar Spheres NF, 20–25 mesh | 167.29 g |
| Povidone USP | 5.10 g |
| Spray Talc | 25.51 g |
| Purified Water USP* | q.s. or 258.50 mL |
| IR Film Coating | |
| Hydroxypropyl Methylcellulose 2910 USP | 3.73 g |
| Polyethylene Glycol 3350 NF | 0.62 g |
| Spray Talc | 0.62 g |
| Purified Water USP* | q.s. or 57.50 mL |
| Total Weight | 253.89 g |
| No. 2 Hard Gelatin Capsules | 1000 |

*Purified Water USP is used in the manufacturing process, but is removed during drying.

Formulation No. 38
(Enteric Release (ER) Pellets in CR2 Capsule)
Label Claim: 40 mg (as base)

| | Amount/1000 Capsules |
|---|---|
| Core Pellets | |
| Tacrine Hydrochloride Monohydrate | 51.02 g |
| Sugar Sphered NF, 20–25 mesh | 167.29 g |
| Povidone USP | 5.10 g |
| Spray Talc | 25.51 g |
| Purified Water USP* | q.s. or 258.50 mL |
| Enteric Coating | |
| Eudragit L30D (30% solids) | 99.55 g |
| Triethyl Citrate FCC | 7.47 g |
| Spray Talc | 1.87 g |
| Purified Water USP* | q.s. or 140.00 mL |
| Total Weight | 288.12 g |
| No. 2 Hard Gelatin Capsules | 1000 |

*Purified Water USP is used in the manufacturing process, but is removed during drying.

Formulation No. 39
(Sustained Release (SR1) Pellets in CR3 Capsule)
Label Claim 40 mg (as base)

| | Amount/1000 Capsules |
|---|---|
| Core Pellets | |
| Tacrine Hydrochloride Monohydrate | 51.02 g |
| Sugar Spheres NF, 20–25 mesh | 167.29 g |
| Povidone USP | 5.10 g |
| Spray Talc | 25.51 g |
| Purified Water USP* | q.s. or 258.50 mL |
| Sustained Coating | |
| Ethylcellulose Dispersion NF (30% solids) | 93.62 g |
| Triethyl Citrate FCC | 7.02 g |
| Spray Talc | 0.37 g |
| Hydroxypropyl Methylcellulose 2910 USP | 1.87 g |
| Purified Water USP* | q.s. or 146.17 mL |
| Overcoat Coating | |
| Hydroxypropyl Methylcellulose 2910 USP | 2.15 g |
| Polyethylene Glycol 3350 NF | 0.36 g |
| Spray Talc | 0.36 g |
| Purified Water USP* | q.s. or 32.92 mL |
| Total Weight | 289.14 g |
| No. 2 Hard Gelatin Capsules | 1000 |

*Purified Water USP is used in the manufacturing process, but is removed during drying.

Formulation No. 40
(Sustained Release (SR2) Pellets in CR4 Capsule)
Label Claim 40 mg (as base)

| | Amount/1000 Capsules |
|---|---|
| Core Pellets | |
| Tacrine Hydrochloride Monohydrate | 51.02 g |
| Sugar Spheres NF, 20–25 mesh | 167.29 g |
| Povidone USP | 5.10 g |
| Spray Talc | 25.51 g |
| Purified Water USP* | q.s. or 258.50 mL |
| Sustained Coating | |
| Ethylcellulose Dispersion NF (30% solids) | 94.79 g |
| Triethyl Citrate FCC | 8.53 g |
| Spray Talc | 0.37 g |
| Purified Water USP* | q.s. or 145.29 mL |
| Overcoat Coating | |
| Hydroxypropyl Methylcellulose 2910 USP | 2.15 g |
| Polyethylene Glycol 3350 NF | 0.36 g |
| Spray Talc | 0.36 g |
| Purified Water USP* | q.s. or 32.92 mL |
| Total Weight | 289.13 g |
| No. 2 Hard Gelatin Capsules | 1000 |

*Purified Water USP is used in the manufacturing process, but is removed during drying.

Formulation No. 41
(Sustained Release (SR3) Pellets in CR5 Capsule)
Label Claim 40 mg (as base)

| | Amount/1000 Capsules |
|---|---|
| Core Pellets | |
| Tacrine Hydrochloride Monohydrate | 51.02 g |
| Sugar Spheres NF, 20–25 mesh | 167.29 g |

Formulation No. 41
(Sustained Release (SR3) Pellets in CR5 Capsule)
Label Claim 40 mg (as base)

| | Amount/1000 Capsules |
|---|---|
| Povidone USP | 5.10 g |
| Spray Talc | 25.51 g |
| Purified Water USP* | q.s. or 258.50 mL |
| Sustained Coating | |
| Ethylcellulose Dispersion NF (30% solids) | 157.97 g |
| Triethyl Citrate FCC | 14.22 g |
| Spray Talc | 0.62 g |
| Purified Water USP* | q.s. or 242.09 mL |
| Overcoat Coating | |
| Hydroxypropyl Methylcellulose 2910 USP | 2.33 g |
| Polyethylene Glycol 3350 NF | 0.39 g |
| Spray Talc | 0.39 g |
| Purified Water USP* | q.s. or 35.77 mL |
| Total Weight | 289.13 g |
| No. 2 Hard Gelatin Capsules | 1000 |

*Purified Water USP is used in the manufacturing process, but is removed during drying.

Formulation No. 42
(Immediate and Enteric Release Pellets in CR6 Capsule)
Label Claim 40 mg (as base)

| | Amount/1000 Capsules | |
|---|---|---|
| Immediate Release Pellets | | |
| Core Pellets, composed of | | 124.46 g |
| Tacrine Hydrochloride Monohydrate | 25.510 g | |
| Sugar Spheres NF, 20–25 mesh | 83.645 g | |
| Povidone USP | 2.550 g | |
| Spray Talc | 12.755 g | |
| Purified Water USP* | q.s. or 129.250 mL | |
| IR Film Coating, composed of | | 2.49 g |
| Hydroxypropyl Methylcellulose 2910 | 1.87 g | |
| Polyethylene Glycol 3350 NF | 0.31 g | |
| Spray Talc | 0.31 g | |
| Purified Water USP* | q.s. or 28.75 mL | |
| Enteric Release Pellets | | |
| Core Pellets, composed of | | 124.46 g |
| Tacrine Hydrochloride Monohydrate | 25.510 g | |
| Sugar Spheres NF, 20–25 mesh | 83.645 g | |
| Povidone USP | 2.550 g | |
| Spray Talc | 12.755 g | |
| Purified Water USP* | q.s. or 129.250 mL | |
| Enteric Coating, composed of | | 19.60 g |
| Eudragit L30D (30% 0 solids) | 49.79 g | |
| Triethyl Citrate FCC | 3.73 g | |
| Spray Talc | 0.93 g | |
| Purified Water USP* | q.s. or 70.00 mL | |
| Total Weight | | 271.01 g |
| No. 2 Hard Gelatin Capsules | | 1000 |

*Purified Water USP is used in the manufacturing process, but is removed during drying.

Manufacturing Process

The following manufacturing procedures describe the preparation of the core pellets, the various film coating procedures for each formulation, and the encapsulation of the coated pellets.

Manufacture of Core Pellets a. Dissolve the povidone in about 20 percent of the total required purified water.

b. Dissolve the tacrine hydrochloride monohydrate in the remaining water.

c. Add the solution from step a into the solution from step b and stir.

d. Add the spray talc into the mixture from step c and continue stirring.

e. Load the sugar spheres into fluid-bed tangential coating equipment and spray on the mixture from step d.

f. Dry the core pellets by fluidization for about 5 minutes immediately following step e or tray dry in a forced-air oven.

g. Separate and retain the 16–20 mesh fraction.

Core Pellets Coating

Formulation 37 a. Dissolve the hydroxypropyl methylcellulose and the polyethylene glycol in purified water using a stirrer.

b. Add the spray talc to the solution from step a and continue stirring.

c. Load the core pellets into fluid-bed tangential coating equipment and apply the coating mixture from step b.

Formulation 38 a. Disperse the triethyl citrate in purified water using a stirrer.

b. Add the Eudragit L3OD to the solution from step a and continue stirring for at least 15 minutes.

c. Add the spray talc to the mixture from step b and continue stirring.

d. Load the core pellets into fluid-bed tangential coating equipment and apply the coating mixture from step c.

Formulation 39 a. For the sustained release coating preparation, dissolve the hydroxypropyl methylcellulose in about 10 percent of the total volume of purified water using a stirrer.

b. Disperse the triethyl citrate in the remaining purified water using a stirrer.

c. Add the ethylcellulose dispersion to the solution from step b and continue stirring for at least 30 minutes.

d. Add the solution from step a and the spray talc to the mixture from step c and continue stirring.

e. For the overcoating preparation, dissolve the hydroxypropyl methylcellulose and the polyethylene glycol in the purified water using a mixer, then add the spray talc and continue stirring.

f. Load the core pellets into fluid-bed tangential coating equipment and apply the sustained release coat preparation from step d.

g. Apply the overcoat preparation from step e using the same fluid-bed tangential coating equipment.

h. Upon completion of step g, continue the fluidization for about 30 to 60 minutes at 60° C. product temperature.

Formulations 40 and 41 a. For the sustained release coating preparation, disperse the triethyl citrate in the purified water using a stirrer.

b. Add the ethylcellulose dispersion to the solution from step a and continue stirring for at least 30 minutes.

c. Add the spray talc to the mixture from step b and continue stirring.

d. Prepare the overcoat by dissolving the hydroxypropyl methylcellulose and polyethylene glycol in the purified water using a stirrer, then adding the spray talc and continue stirring.

e. Load the core pellets into fluid-bed tangential coating equipment and apply the sustained coating preparation from step c.

f. Using the same fluid-bed tangential coating equipment, apply the overcoat preparation from step d.

g. Upon completion of step f, continue fluidization for about 30 to 60 minutes at 60° C. product temperature.

Formulation 42 a. Film coat a portion of the core pellets according to the procedure used for Formulation 37.

b. Enteric coat another portion of the core pellets according to the procedure used for Formulation 38.

c. Blend the coated pellets from step a and step b at a ratio to contain equal quantities of tacrine base.

Formulation 43 a. Film coat a portion of the core pellets according to the procedure used for Formulation 37.

b. Sustain coat another portion of the core pellets according to the procedure used for Formulation 39.

c. Blend the coated pellets from step a and step b at a ratio to contain equal quantities of tacrine base.

Encapsulation a. Encapsulate the amount of pellets listed in Table 2 into hard gelatin capsules using a capsule filling machine with pellet filler attachment.

b. The total yield of product is calculated by determining the total unit count and comparing it to the yield, theoretically expected from the batch formula.

TABLE 2

| Theoretical Capsule Fill Weights | |
|---|---|
| Formulation No. | Fill Weight* |
| Formulation 37 (IR Pellets) | 254 mg |
| Formulation 38 (ER Pellets) | 288 mg |
| Formulation 39 (SR1 Pellets) | 289 mg |
| Formulation 40 (SR2 Pellets) | 289 mg |
| Formulation 41 (SR3 Pellets) | 314 mg |
| Formulation 42 (IR + ER Pellets) | 271 mg |
| Formulation 43 (IR + SR3 Pellets) | 284 mg |

*Target fill weight may vary (± 10% tentative) based on the in-process coated pellets assay.

EXAMPLES 8–10

The following examples were carried out to develop controlled release pellet formulations for tacrine hydrochloride monohydrate that reduce the dosing frequency to improve convenience and patient compliance and in which the drug loading was 50% greater than that reported for Examples 1–7. Core pellets containing tacrine hydrochloride monohydrate were manufactured using fluid-bed tangential coating equipment.

The drug pellets were coated in a fluid-bed rotor granular with aqueous dispersions containing ethylcellulose to form sustaining coats. The coating dispersions contained 36.1%, 34.5% and 33.2% (w/w) Aquacoat for the formulations designated as CR8, CR9 and CR10, respectively. The insoluble, film-forming polymer, ethylcellulose in Aquacoat, provides a diffusion barrier for tacrine and controls its release rate from the drug laden pellets. The coating dispersions also contained 0.6%, 1.0% and 1.4% w/w hydroxypropyl methylcellulose for CR8, CR9 and CR10, respectively. Hydroxypropyl methylcellulose, a water-soluble polymer was incorporated in the coating dispersions to increase the permeability of the sustaining coat. In addition, all the coating dispersions contain 3.4% w/w triethyl citrate, a plasticizing agent for ethylcellulose, 0.15% w/w mistron spray talc, an antiadherent, and 0.05% w/w antifoam emulsion.

The coated pellets for CR8, CR9 and CR10 were subsequently overcoated with an aqueous dispersion containing 5.2% w/w hydroxypropyl methylcellulose. 0.9% w/w polyethylene glycol 3350, 0.9% w/w mistron spray talc, and 0.04% w/w antifoam emulsion. This overcoat prevents pellets from sticking and reduces attrition during handling and storage. The finished pellets were cured by fluidization at 60° C. for one hour in the coating equipment immediately following the overcoat process in order to promote film coalescence.

The following table describes the product references made throughout this section.

| Formulation | Dissolution Profile of Pellets in Formulation |
|---|---|
| CR8 (53) | Sustained Release |
| CR9 (54) | Sustained Release |
| CR10 (55) | Sustained Release |

Collectively these products are referred as control release capsules.

Quantitative Formula for the Capsule Products

The quantitative formulations set out below show the amounts of ingredients per 1000 capsules. The equipment and parameters (e.g., size and brand of equipment, parameters used in preparation of core drug pellets as well as in coating the pellets, etc.) listed in the manufacturing directions are based on the batches made.

| Formulation No. 53 in CR8 Capsule Label Claim 40 mg (as base) | |
|---|---|
| | Amount/1000 Capsules |
| Core Pellets | |
| Tacrine Hydrochloride Monohydrate | 51.02 g[1] |
| Sugar Sphered NF, 20–25 mesh | 96.75 g |
| Povidone USP | 4.00 g |
| Spray Talc | 12.75 g |
| Antifoam Emulsion | 0.06 g |
| Purified Water USP* | q.s. or 249.10 mL |
| Coating | |
| Sustained Coating | |
| Ethylcellulose Dispersion NF (30% solids) | 14.23 g[2] |
| Triethyl Citrate FCC | 4.50 g |
| Spray Talc | 0.20 g |

Formulation No. 53 in CR8 Capsule
Label Claim 40 mg (as base)

|  | Amount/1000 Capsules |
|---|---|
| Hydroxypropyl Methylcellulose 2910 USP | 0.75 g |
| Antifoam Emulsion | 0.07 g |
| Purified Water USP* | q.s. or 78.68 mL |
| Overcoat Coating |  |
| Hydroxypropyl Methylcellulose 2910 USP | 1.38 g |
| Polyethylene Glycol 3350 NF | 0.23 g |
| Spray Talc | 0.23 g |
| Antifoam Emulsion | 0.01 g |
| Purified Water USP* | q.s. or 24.43 mL |
| Total Weight | 186.18 g |
| No. 3 Hard Gelatin Capsules | 1000 |

[1]Equivalent to 40.00 mg tacrine base per capsule.
[2]Solids weight.
*Purified Water USP is used in the manufacturing process, but is removed during drying.

Formulation No. 54 in CR9 Capsule
Label Claim 40 mg (as base)

|  | Amount/1000 Capsules |
|---|---|
| Core Pellets |  |
| Tacrine Hydrochloride Monohydrate | 51.02 g[1] |
| Sugar Spheres NF, 20–25 mesh | 96.75 g |
| Povidone USP | 4.00 g |
| Spray Talc | 12.75 g |
| Antifoam Emulsion | 0.06 g |
| Purified Water USP* | q.s. or 249.10 mL |
| Coating |  |
| Sustained Coating |  |
| Ethylcellulose Dispersion NF (30% solids) | 13.63 g[2] |
| Triethyl Citrate FCC | 4.50 g |
| Spray Talc | 0.20 g |
| Hydroxypropyl Methylcellulose 2910 USP | 1.35 g |
| Antifoam Emulsion | 0.07 g |
| Purified Water USP* | q.s. or 78.68 mL |
| Overcoat Coating |  |
| Hydroxypropyl Methylcellulose 2910 USP | 1.38 g |
| Polyethylene Glycol 3350 NF | 0.23 g |
| Spray Talc | 0.23 g |
| Antifoam Emulsion | 0.01 g |
| Purified Water USP* | q.s. or 24.43 mL |
| Total Weight | 186.18 g |
| No. 3 Hard Gelatin Capsules | 1000 |

[1]Equivalent to 40.00 mg tacrine base per capsule.
[2]Solids weight.
*Purified Water USP is used in the manufacturing process, but is removed during drying.

Formulation No. 55 in CR10 Capsule
Label Claim 40 mg (as base)

|  | Amount/1000 Capsules |
|---|---|
| Core Pellets |  |
| Tacrine Hydrochloride Monohydrate | 51.02 g[1] |
| Sugar Spheres NF, 20–25 mesh | 96.75 g |
| Povidone USP | 4.00 g |
| Spray Talc | 12.75 g |
| Antifoam Emulsion | 0.06 g |
| Purified Water USP* | q.s. or 249.10 mL |
| Coating |  |
| Sustained Coating |  |
| Ethylcellulose Dispersion NF (30% solids) | 13.11 g[2] |
| Triethyl Citrate FCC | 4.50 g |
| Spray Talc | 0.20 g |
| Hydroxypropyl Methylcellulose 2910 USP | 1.87 g |
| Antifoam Emulsion | 0.07 g |
| Purified Water USP* | q.s. or 78.68 mL |
| Overcoat Coating |  |
| Hydroxypropyl Methylcellulose 2910 USP | 1.38 g |
| Polyethylene Glycol 3350 NF | 0.23 g |
| Spray Talc | 0.23 g |
| Antifoam Emulsion | 0.01 g |
| Purified Water USP* | q.s. or 24.43 mL |
| Total Weight | 186.18 g |
| No. 3 Hard Gelatin Capsules | 1000 |

[1]Equivalent to 40.00 mg tacrine base per capsule.
[2]Solids weight.
*Purified Water USP is used in the manufacturing process, but is removed during drying.

The core pellets, film coating, and encapsulation were then carried out according to the procedures described in Examples 1–7.

EXAMPLE 11

Pharmacokinetic Evaluation of Controlled Release Formulations CR1, CR3, CR4, and CR5

Controlled release (CR) formulations were prepared by coating immediate release (IR) core pellets, designated as CR1, with a sustained release (SR) polymer system. Rate of tacrine release rate from CR1 in vitro was very rapid (100% in 10 minutes) and similar to the release rate from market tacrine capsules. In vivo performance of CR1 was expected to be representative of performance of tacrine market capsules. The SR coatings were combinations of a water soluble polymer (hydroxypropylmethylcellulose; HPMC) and a water-insoluble polymer (Aquacoat, ethylcellulose). Relative amounts of the two polymers and the coating levels were varied to prepare three prototype formulations (CR3, CR4 and CR5, Table 3) with different tacrine release rates in vitro (release rate: CR3>CR4>CR5). Dissolution studies showed a lag-time (time preceding the first quantifiable concentration) in the following order CR5>CR4>CR3.

Pharmacokinetics of CR3, CR4, and CR5 were compared to those of the core pellets to determine the effect of the SR formulation composition and coating levels. The object of the study was to determine the relative bioavailability and in vivo release characteristics of CR1 and the three 40 mg prototype capsules, CR3, CR4, and CR5, to aid in the development of a tacrine CR formulation. Sixteen healthy volunteers received a single 40-mg tacrine dose, as either one CR1, CR3, CR4, or CR5 capsule according to a randomized, 4-way crossover design (Table 3). Subjects ranged in age form 50 to 74 years (mean=62). None of the subjects were smokers. Serial blood samples were drawn up to 24 hours following each dose and subsequently analyzed for tacrine.

TABLE 3

Tacrine Capsule Formulations Used in Protocol 970-36

| Formula | In vitro release profile | SR Polymer composition | Coating (% w/w*) | Dose (mg) | Code |
|---|---|---|---|---|---|
| 37 | Immediate Release (IR) | NA | NA | 40 | CR1 |
| 39 | Sustained Release (SR1) | Aquacoat HPMC | 15 | 40 | CR3 |
| 40 | Sustained Release SR2) | Aquacoat | 15 | 40 | CR4 |
| 41 | Sustained Release (SR3) | Aquacoat | 25 | 40 | CR5 |

*Increase in core pellet weight during coating.
NA-not applicable.

Figure 3:
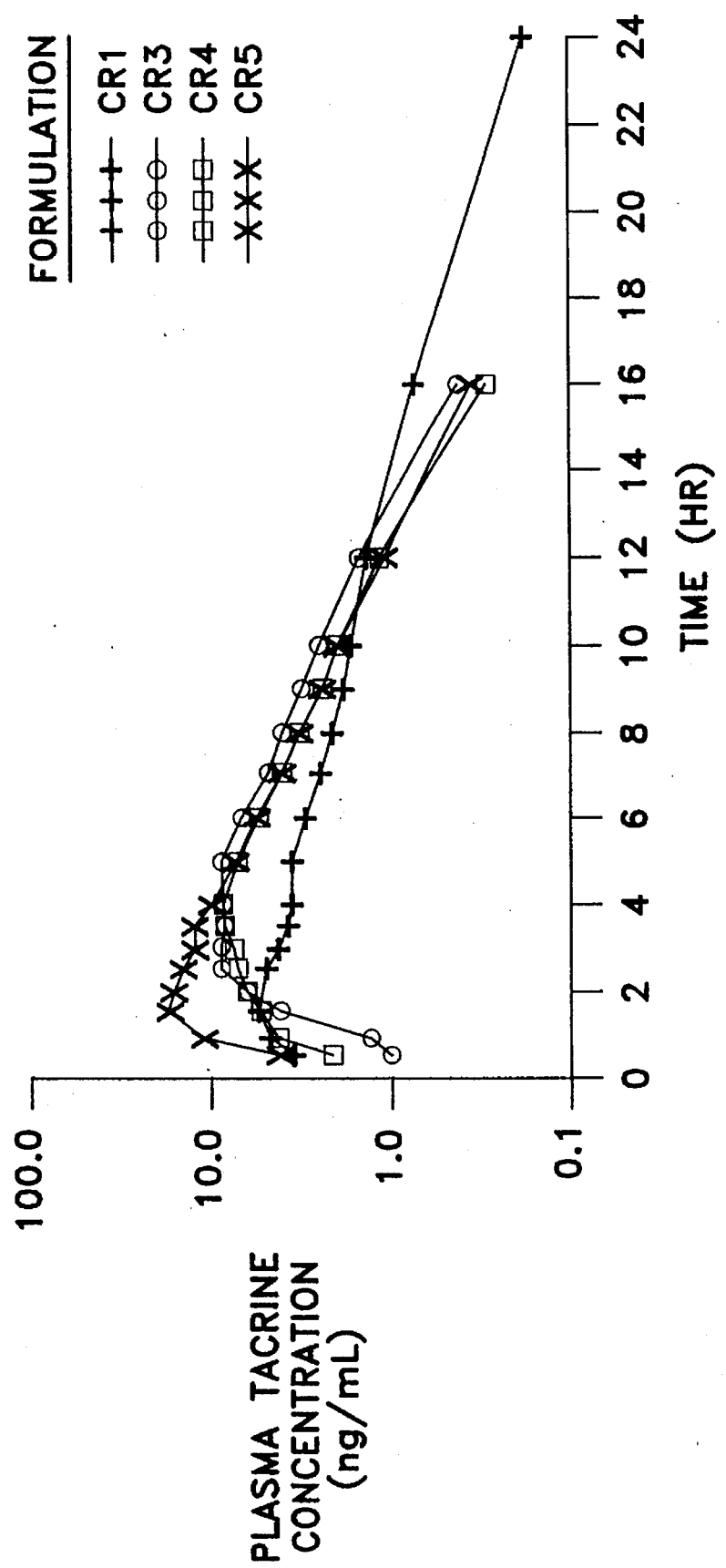
FIG. 3 is a graph showing the mean plasma 1-OH tacrine concentrations following administration of single 40 mg doses of tacrine CR capsules (CR1, CR2, CR6, and CR7) to healthy elderly volunteers. Top: semi-logarithmic scale; Bottom: linear scale.
Figure 3A:
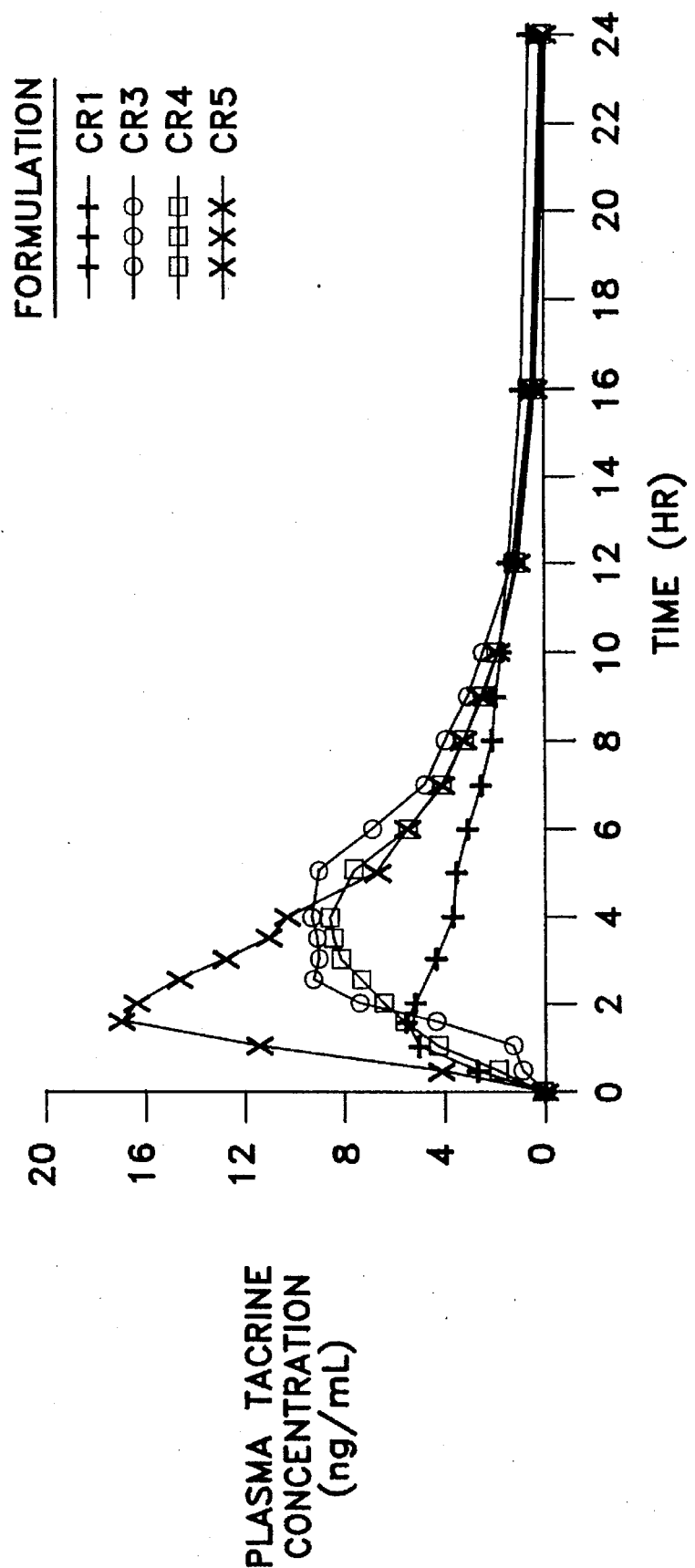
Figure 4:
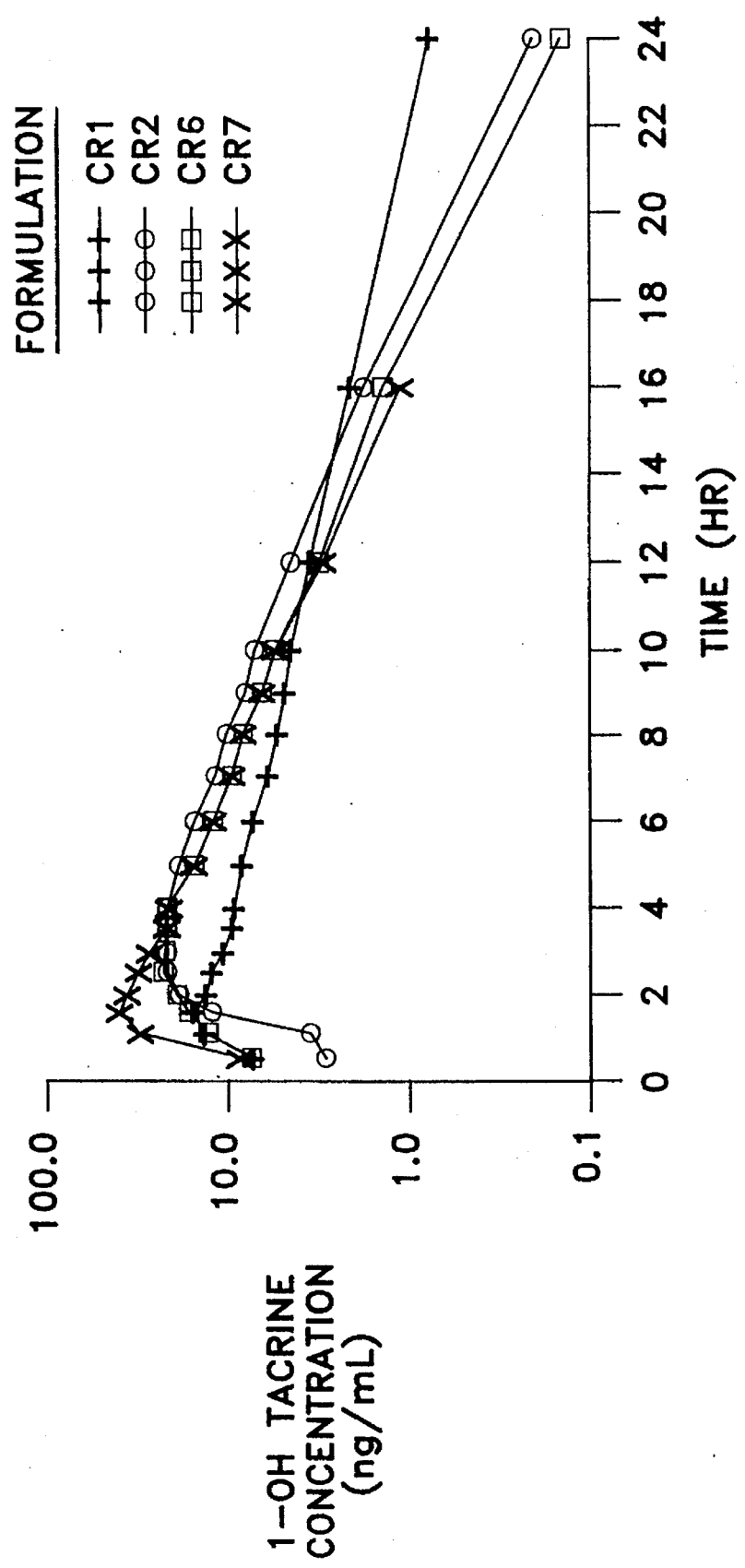
FIG. 4 is a graph showing the mean plasma 1-OH tacrine concentrations following administration of single 40 mg doses of tacrine CR capsules (CR1, CR2, CR6, and CR7) to healthy elderly volunteers. Top: semi-logarithmic scale; Bottom: linear scale.
Figure 4A:
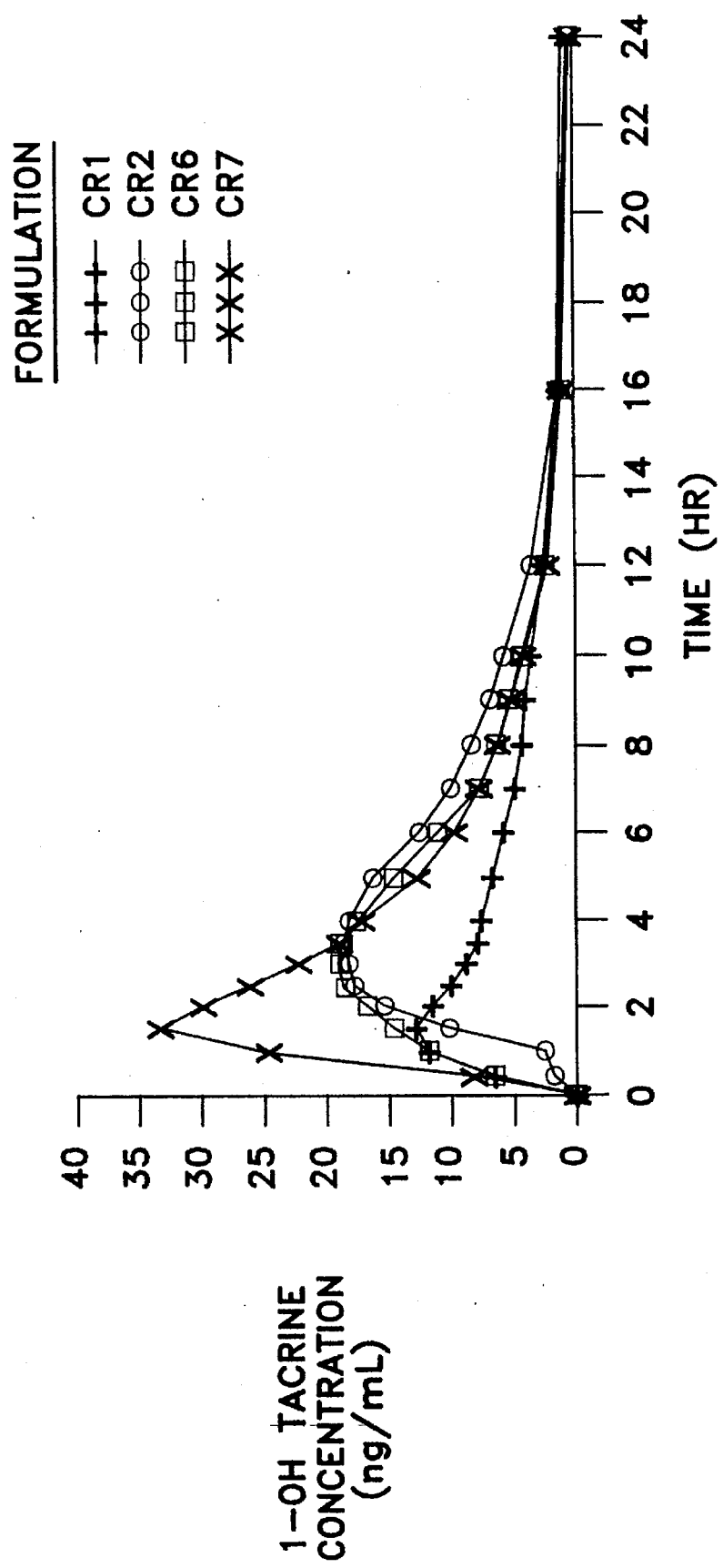

Treatment mean plasma concentration versus time profiles for tacrine and 1-OH tacrine are shown in FIG. 3 and FIG. 4, respectively. A summary of Pharmacokinetics and statistical results is presented in Table 4. Inspection of pharmacokinetic data from a bioequivalence study for tacrine market capsules indicated that CR1 pharmacokinetics observed in the present study were similar to and thus representative of those for the market capsule.

Mean plasma profiles for CR3, CR4, and CR5 were distinguishable from each other and from that for CR1 (FIG. 3). Tacrine absorption from formulations CR3, CR4, and CR5 was controlled (slowed) relative to CR1 as demonstrated by increased tmax values, decreased Cmax values, and relatively high plasma concentrations at 12, 16 and 24 hours. The pattern of sustained release observed among formulations in mean profiles was consistently observed for individual subjects. Terminal rate constant (Lambda z) values were significantly lower for the three CR capsule prototypes than that for CR1 and indicated that absorption rate was limited by rate of tacrine release from the CR formulation. Thus, these z values reflected the absorption rate rather than the rate of elimination ("flip-flop" kinetics). Results indicated that in vivo tacrine release rates decreased in the same order (CR3>CR4>CR5) as observed in vitro.

Lag-time (tlag) between dose administration and apparent start of absorption was determined as the sampling time immediately preceding time of the first quantifiable plasma concentration. As the apparent absorption rate decreased, tlag values increased. Mean tlag values ranged from 0.8 hour for CR3 to 3.1 hour for CR5. The same rank order was observed with dissolution test data and provided further evidence that release from the CR formulation was rate limiting. Inter-subject variability (% RSD) was remarkably low for tmax, tlag and Lambda z for all four formulations. Low variability in tmax, Lambda z and tlag values was consistent with formulation controlled pharmacokinetics. (Table 4).

Extent of absorption was assessed by evaluation of AUC(0-tldc) values. A corresponding decrease in extent of absorption was observed with decrease in Lambda z. Based on mean values of AUC(0-tldc) ratios, bioavailability of CR3, CR4, and CR5 relative to CR1 was 75%, 58%, and 56%, respectively (Table 5). Relative extent of absorption values based on AUC(0-∞) values were similar to those based on AUC(0-tldc).

Inter-subject variability for Cmax and AUC(0-tldc) was high (%RSD=40–60%) for all CR formulations. This variability was not attributable to the formulations themselves because high variability was also observed with CR1 and with other dosage forms in previous tacrine studies. High variability in Cmax and AUC(0-tldc) values suggests that individuals differ markedly with respect to how much tacrine is absorbed. Saturable first-pass tacrine metabolism and intersubject variation in absorption, metabolism, and/or volume of distribution may have contributed to this variability. Pharmacokinetic data following an intravenous dose would be required to determine the source of variability.

Plasma 1-OH tacrine concentrations were approximately two times higher than those for tacrine for all of the formulations. The 1-OH tacrine concentration versus time profiles (FIG. 4) parallel those for tacrine. This result suggests that 1-OH tacrine pharmacokinetics are also controlled by rate of release from the CR formulation.

In summary, pharmacokinetics for single-dose administration of prototype 40-mg capsule formulations CR3, CR4, and CR5 indicate controlled release of tacrine. Relative absorption rates in vivo reflect relative tacrine rates in dissolution tests. Bioavailability of CR3, CR4, and CR5 capsules is 75%, 58%, and 56% relative to that of CR1, an immediate release dosage form.

TABLE 4

Mean Tacrine Pharmacokinetic Parameter Values for Administration of Single 40-mg Doses of Tacrine CR Capsules to 16 Healthy Elderly Volunteers Treatment Mean (% RSD) Value

| Parameter | CR1 | CR3 | CR4 | CR5 |
|---|---|---|---|---|
| Cmax | 16.4 (38.4) | 7.8 (48.5) | 5.3 (50.1)[a] | 4.0 (40.3)[a] |
| tmax | 2.0 (19.0) | 5.1 (13.5) | 5.7 (15.4) | 6.4 (22.8) |
| tlag | 0 | 0.08 (36) | 1.8 (23) | 3.1 (12) |
| AUC (0-tldc) | 89 (49.8) | 61 (52.8)[a] | 51 (63.4)[a,b] | 44 (47.1)[b] |
| AUC (0-∞) | 92 (48.2) | 69 (48.5)[a] | 61 (55.9)[a] | 60 (41.2)[a] |
| Lambda Z | 0.274 (19.0) | 0.174 (34.6) | 0.110 (34.3)[a] | 0.074 (27.9)[a] |
| t½ | 2.5 | 4.0 | 6.3 | 9.4 |

[a,b]For a given parameter, mean values are significantly different unless they share a common letter (alpha = 0.05). Differences between treatment mean t½ values were not evaluated statistically.

TABLE 5

Means of Individual Subject Parameter Ratios
Mean Ratio (% RSD)

| Parameter | CR3/CR1 | CR4/CR1 | CR5/CR1 |
|---|---|---|---|
| Cmax | 0.49 (43.3) | 0.33 (26.5) | 0.27 (54.9) |
| tmax | 2.6 (25.5) | 2.9 (31.1) | 3.2 (27.9) |
| AUC (0-tldc) | 0.75 (48.9) | 0.58 (38.2) | 0.56 (58.7) |
| AUC (0-∞) | 0.80 (48.7) | 0.64 (31.2) | 0.73 (55.7) |

Cmax = Maximum observed plasma concentration (ng/mL)
tmax = Time of Cmax (hour)
tlag = Sampling time immediately preceding the first quantifiable plasma concentration (hour)
AUC (0-tldc) = Area under the plasma concentration-time from time 0 to time of last detectable concentration (ng*hour/mL)
AUC (0-infinity) = Area under the plasma concentration time from time 0 to infinite time (ng*hour/mL)
Lambda Z = Terminal phase rate constant (1/hour)
t½ = Half-life (hour) (harmonic mean)

1. J. Skelly, G. Amidon, W. Barr et all, In Vivo Testing and Correlation for Oral Controlled/Modified-Release Dosage Forms, Pharmaceutical Research, Vol. 7, No. 9 p 975–982, 1990.

EXAMPLE 12

Pharmacokinetic Evaluation of Controlled Release Formulations CR1, CR2, CR6, and CR7

Controlled-release (CR) formulations were prepared by coating immediate-release (IR) core pellets, designated as CR1, with a sustained-release (SR) or enteric-release (ER) polymer system. Rate of tacrine release from CR1 in vitro was very rapid (100% in 10 minutes) and similar to the release rate from market tacrine capsules. In vivo performance of CR1 was expected to be representative of performance of tacrine market capsules.

The ER system was designed to provide pH dependent drug release by means of a polymethacrylate copolymer. Release of tacrine from the ER formulation was minimal (<3% in 2 hours) in acidic media and rapid (>95% in 15 minutes) at pH 6.8. ER pellets were designed to delay tacrine release until the pellets reached the small intestine. Capsules containing only ER pellets (CR2) and capsules containing equal pans of IR and ER pellets (CR6) were prepared.

The SR system, designated SR3, entailed coating IR pellets with a water-insoluble polymer (Aquacoat; ethylcellulose). Dissolution studies indicated slow release of tacrine from the SR3 pellets, as well as a lag-time of 1 to 2 hours. Capsules filled entirely with SR3 pellets represented the slowest releasing formulation tested in the preceding study (970–36). Capsules, designated as CR7, containing equal pans of IR and SR3 pellets were prepared for evaluation in the present study.

The study objective was to determine the relative bioavailability and in vivo release characteristics of a 40-mg tacrine IR capsule (CR1) and three prototype 40-mg tacrine CR capsules (CR2, CR6 and CR7) to aid in the development of a tacrine controlled-release formulation. Sixteen healthy volunteers received a single 40-mg tacrine dose of CR1, CR2, CR6, or CR7 according to a randomized, 4-way crossover design (Table 6). Subjects ranged in age from 59 to 77 years (mean=67). Subject 10 was the only smoker. Serial blood samples were drawn up to 24 hours following each dose and were subsequently analyzed for tacrine, 1-OH tacrine, 2-OH tacrine, and 4-OH tacrine. Results for tacrine and 1-OH tacrine for 15 subjects are discussed herein.

TABLE 6

Tacrine Capsule Formulations

| Formulation Number | Type of Pellets in Capsule | Dose (mg) | Treatment Code |
|---|---|---|---|
| 37 | Immediate-Release (IR) | 40 | CR1 |
| 38 | Enteric-Release (ER) | 40 | CR2 |
| 42 | Immediate and Enteric Release (20 mg IR + 20 mg IR) | 40 | CR6 |
| 43 | Immediate and Sustained Release (20 mg IR + 20 mg SR3) | 40 | CR7 |

Treatment mean plasma concentration versus time profiles for tacrine and 1-OH tacrine are shown in FIG. 3 and FIG. 4, respectively. A summary of pharmacokinetic and statistical results is presented in Table 7. CR1 pharmacokinetics were similar to those for the market capsule as indicated by comparison with data from a bioequivalence study for tacrine market capsules.

The mean concentration-time profile for CR2 was distinguishable from that for CR1. Differences between individual concentration-time profiles were remarkably large for CR2, and therefore, the mean profile was not representative of that for any given subject. A major source for variability appeared to be the time between dose administration and apparent start of absorption (flag). Mean flag was 1.0 hour for CR2, and intersubject variability (%RSD) m this parameter was 85%. After adjustment for flag, the mean tmax value for CR2 was similar to that for CR 1. Mean Lambda z values for CR2 and CR1 were also similar. Together, these results indicated that CR2 and CR1 had similar absorption and elimination rates and were consistent with pH dependent (enteric) release. The high intersubject variability may have been due to differences in gastric transit time and gastrointestinal tract pH.

Cmax values for CR2 were lower than those for CR1 and suggested lower bioavailability of CR2 as compared to CR1. Extent of absorption was assessed by evaluation of AUC(0-tldc) values and indicated that the bioavailability of CR2 was 82% relative to that of CR1. Results based on AUC(0-∞) values were similar indicating 86% relative bioavailability.

The mean concentration-time profile for CR6 was distinguishable from that for CR1. Differences between individual concentration-time profiles were remarkably large for CR6 and therefore the mean profile was not representative of that for any given subject. Immediate release of tacrine from the IR component of CR6 was apparent in that there was no flag for CR6. With the exception to flag values, pharmacokinetics for CR2 and CR6 were similar to one another. Extent of absorption for CR6, based on AUC(0-tldc) values, was 75% compared to that of CR1. The pharmacokinetics of CR6 were more similar to those for CR2 than expected for a composite of CR1 and CR2. In other words, CR6 pharmacokinetics were not a simple linear combination of those for CR1 and CR2. Lack of consistent performance suggests that both ER formulation (CR2 and CR6) have limited potential as CR dosage forms.

The mean profile for the CR7 capsule was distinguishable from that for CR1. Tacrine absorption from CR7 was controlled relative to CR1 as demonstrated by relatively high plasma concentrations at 12, 16 and 24 hours. Rapid release of tacrine from the IR component of CR7 was apparent in the apparent absence of a flag. The pattern of an initial rise in plasma tacrine concentration after dosing followed by sustained plasma concentrations was consistently observed for individual subjects. The mean Lambda z value for CR7 was significantly lower for CR1 than that for CR7 and was consistent with sustained tacrine release from the SR3 component of CR7. Extent of absorption for CR7, based on AUC(0-tldc) values, was 58% compared to that of CR1. While the pharmacokinetics for CR7 reflected the contribution of each component, they were not a simple combination of those corresponding to pure IR and SR3 as investigated in 970–36.

Intersubject variability for Cmax and AUC values was high (%RSD=70 to 95%) for all four CR formulations. Pharmacokinetics following an intravenous dose would be required to determine the source of variability. Plasma concentrations for 1-OH tacrine were approximately three times higher than those for tacrine for all of the formulations. The 1-OH tacrine concentration versus time profile (FIG. 4) paralleled that for tacrine as was similar for all formulations.

In summary, pharmacokinetics of the three prototype CR formulations and the reference (CR1) capsules are distinct from one another. Results for the enteric coated formulations (CR2 and CR6) are consistent with a pH dependent release. However, these formulations are not suitable for further development because of erratic in vivo performance. Pharmacokinetics of CR6 and CR7 reflect contributions from their two components, but are not simply related to individual component pharmacokinetics. Bioavailability values for CR2, CR6 and CR7 relative to that for CR1 were 82%, 75%, and 58%, respectively.

TABLE 7

Mean Tacrine Pharmacokinetic Parameter Values for
Administration of Single 40-mg Doses of Tacrine CR
Capsules to Healthy Elderly Volunteers
Treatment Mean (% RSD) Value

| Parameter | CR1 | CR3 | CR4 | CR5 |
|---|---|---|---|---|
| Cmax | 17.9 (73.4) | 13.2 (71.4)[a] | 10.3 (79.2)[a] | 6.0 (74.8) |
| tmax | 1.7 (30.6)[a] | 3.2 (35.8)[b] | 3.1 (40.2)[b] | 1.5 (47.1)[a] |
| tlag | 0[a] | 1.0 (85) | 0[a] | 0[a] |
| AUC (0-tldc) | 81 (84.0) | 64 (82.2)[a] | 58 (94.0)[a] | 42 (95.1) |
| AUC (0-∞) | 88 (79.8) | 68 (79.8)[a] | 65 (85.3)[a,b] | 51 (96.0)[b] |
| Lambda Z | 0.29 (36.4)[a] | 0.26 (18.1)[a,b] | 0.30 (23.7)[a] | 0.20 (65.5)[b] |
| t½ | 2.5 | 2.7 | 2.3 | 3.4 |

[a,b]For a given parameter, mean values are significantly different unless they share a common letter (alpha = 0.05). Differences between treatment mean t½ values were not evaluated statistically.

TABLE 8

Means of Individual Subject Parameter Ratios
Mean Ratio (% RSD)

| Parameter | CR2/CR1 | CR6/CR1 | CR7/CR1 |
|---|---|---|---|
| Cmax | 0.77 (22.8) | 0.61 (26.9) | 0.4124 (47.7) |
| tmax | 2.0 (40.8) | 1.9 (46.5) | 0.9 (36.9) |
| AUC (0-tldc) | 0.82 (17.2) | 0.75 (24.3) | 0.58 (40.8) |
| AUC (0-∞) | 0.86 (17.1) | 0.74 (20.1) | 0.67 (26.9) |

Cmax = Maximum observed plasma concentration (ng/mL)
tmax = Time of Cmax (hour)
tlag = Sampling time immediately preceding the first quantifiable plasma concentration (hour)
AUC (0-tldc) = Area under the plasma concentration-time from time 0 to time of last detectable concentration (ng*hour/mL)
AUC (0-infinity) = Area under the plasma concentration time from time 0 to infinite time (ng*hour/mL)
Lambda Z = Terminal phase rate constant (1/hour)
t½ = Half-life (hour) (harmonic mean)

EXAMPLE 13

In vitro/in vivo Correlation of Tacrine CR Capsules

The present study was conducted to understand the relationship between in vitro dissolution of a product and its in vivo performance to minimize human in vivo testing and to discern what limitations the formulation and the drug's pharmacokinetic properties present.

Figure 5:
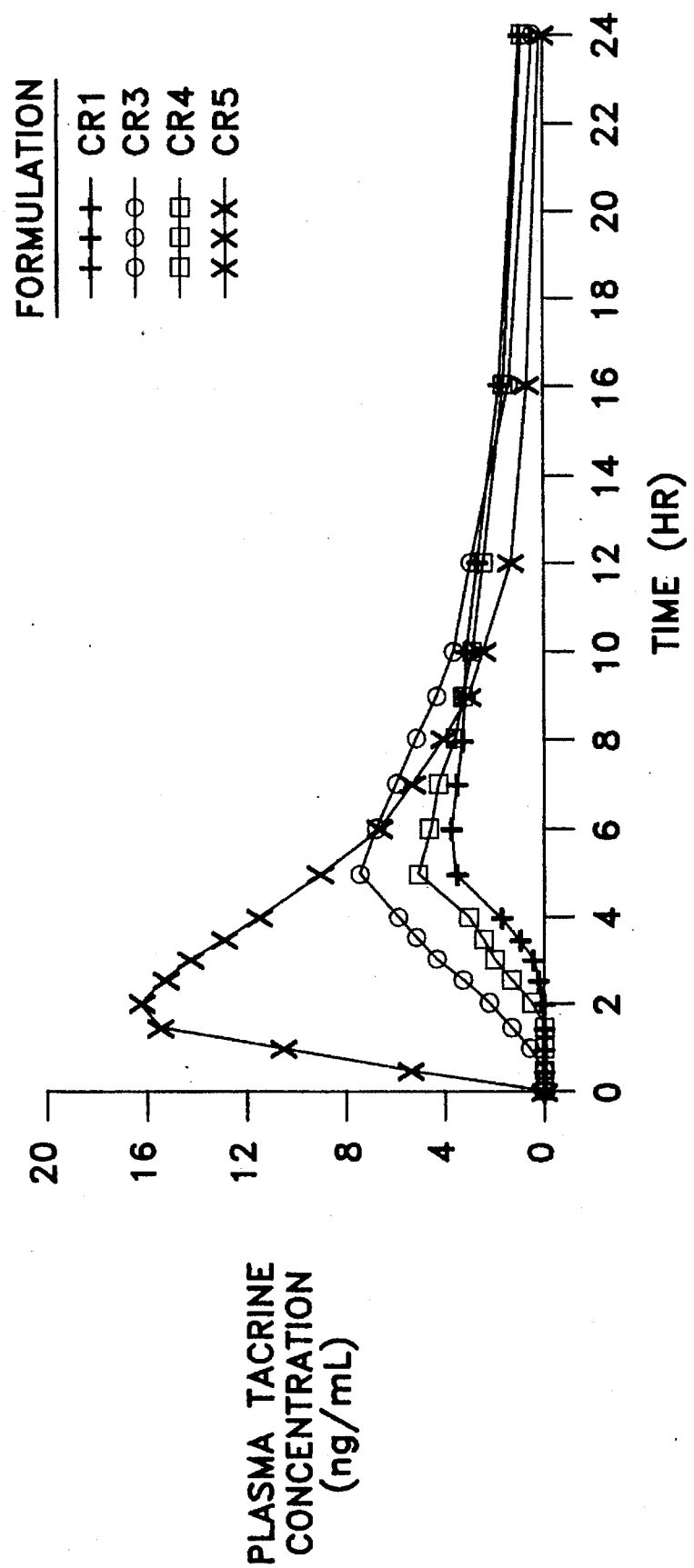
FIG. 5 is a graph showing the mean plasma tacrine concentrations following administration of single 40 mg doses of tacrine CR capsules (CR1, CR3, CR4, and CR5) to healthy elderly volunteers. Top: linear scale; Bottom: semi-logarithmic scale.
Figure 5A:
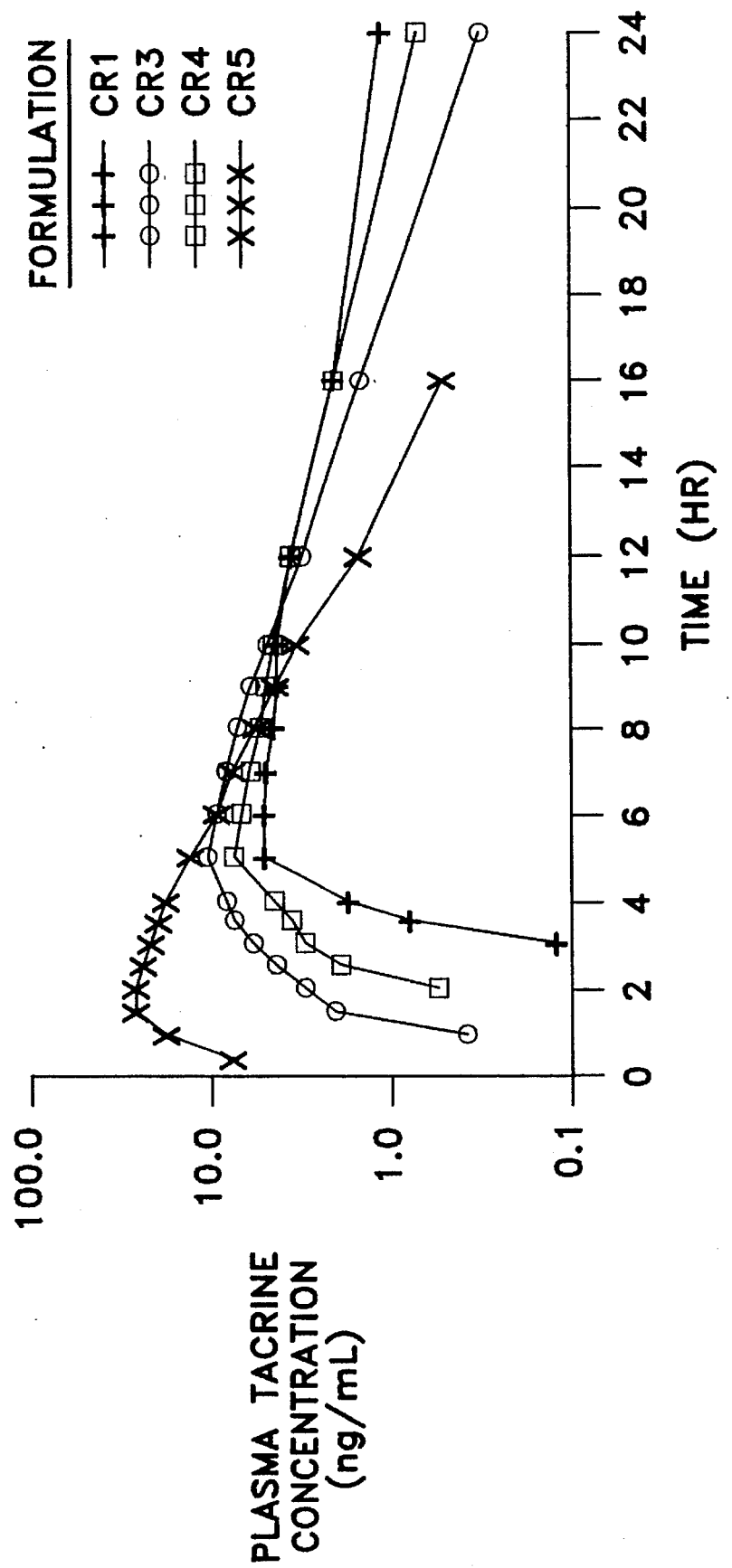

Controlled release (CR) tacrine formulations were prepared by coating immediate release core pellets (CR1) with a sustained release (SR) polymer system. Single doses of three SR formulations (CR3, CR4, and CR5) and CR1 were tested in vivo. Results indicated controlled release of tacrine from CR3, CR4, and CR5, FIG. 5. Absorption was limited by the rate of tacrine release from CR3, CR4, and CR5 ("flip-flop" kinetics). In vivo absorption rates decreased in the same rank order as in vitro tacrine release rates decreased. Also, as absorption rate decreased, bioavailability decreased.

The SR formulation system was further developed with the goal of increasing bioavailability while maintaining sustained release. Tacrine loading of the pellet core was increased by 50% as compared to formulations CR1, CR3, CR4, and CR5 to permit higher doses with smaller capsule sizes.

The objectives of the computations reported herein are: 1) to correlate in vitro dissolution data with in vivo absorption data for tacrine CR formulations; and 2) to predict the in vivo absorption rates of CR8, CR9, and CR10 based on the in vitro/in vivo correlation.

Methods

Absorption rate: For the immediate release formulation, CR1, Wagner-Nelson analysis was performed on individual subject dam. The negative slope of a semi-logarithmic plot of the amount unabsorbed versus time for each subject provided an estimate of the first order rate constant for absorption, $k_A$. For CR3, CR4, and CR5, lambda z values were significantly smaller than those for CR1 indicating that lambda z was $K_A$, and individual lambda z values were used as estimates of $k_A$ values. The average $k_A$ value was determined for each formulation. Mean absorption time (MAT), which reflects the average time for a tacrine molecule to be absorbed, was approximated as the reciprocal of average rate constant (3,4):

$$MAT = 1_{k_A} \quad (1)$$

Figure 6:
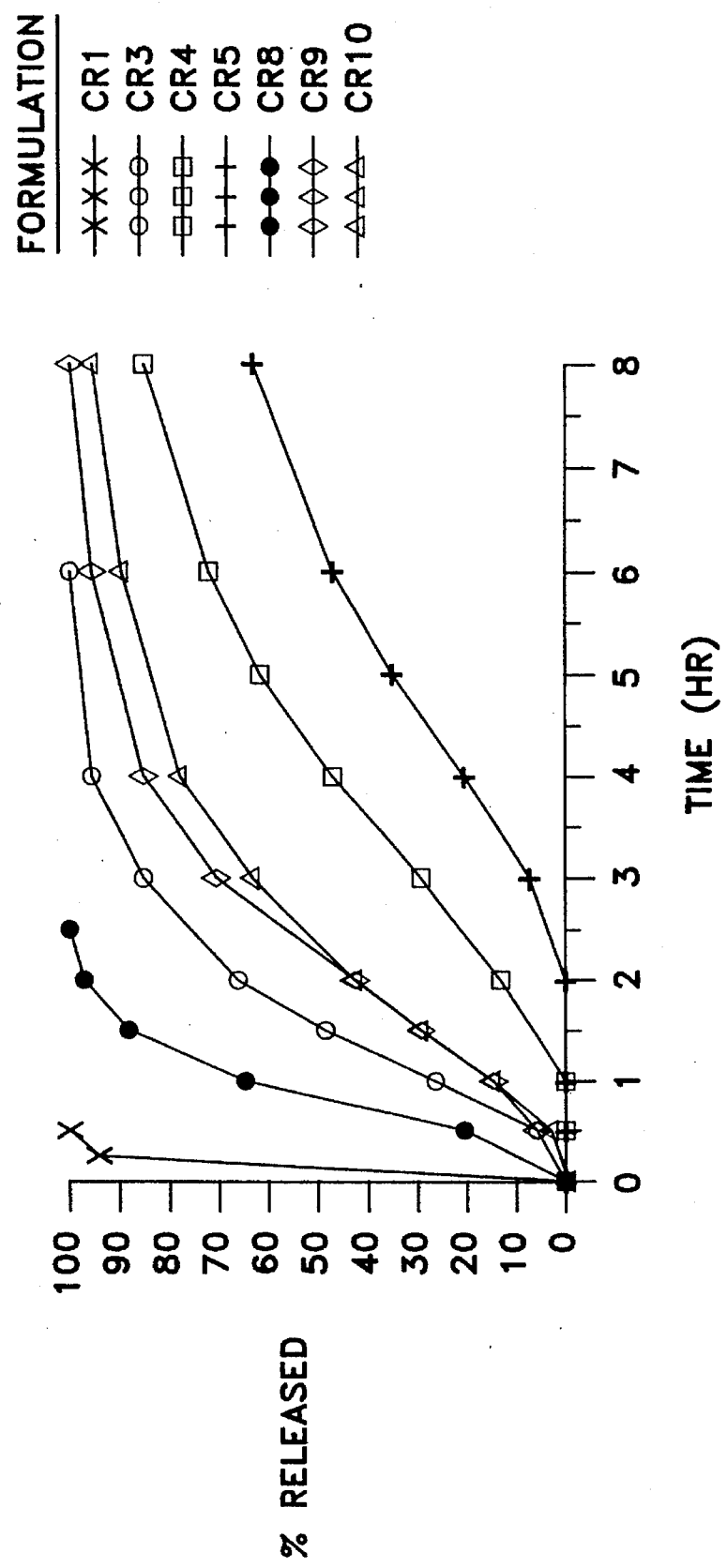
FIG. 6 is a graph showing the percent of dose dissolved as a function of time for seven tacrine formulations (CR1, CR3, CR4, CR5, CR8, CR9, and CR10).

Dissolution rate: Dissolution of tacrine from formulations CR1, CR3, CR4, CR5, CR8, CR9, and CR10 was quantified in water at 37° C. by means of USP apparatus II with paddles rotating at 50 rpm (FIG. 6). Dissolution data for each formulation were characterized by the following equation for first-order drug release occurring after a dissolution lag phase:

$$\text{Percentage Undissolved} = 100\% \cdot \exp(-k_D \cdot \text{time}) \quad (2)$$

where $k_D$ is the first order dissolution rate constant (3,4). The mean dissolution time (MDT), which reflects the average time for a tacrine molecule to dissolve once absorption commences was approximated as (3,4)

$$MDT = 1_{k_D} \quad (3)$$

In vitro/in vivo correlations: Least squared regression was used to characterize an apparent linear relationship between MAT and MDT values corresponding to CR1, CR3, CR4, and CR5. The linear regression parameters were used to predict MAT values from measured MDT values, for formulations CR8, CR9, and CR10. Subsequently, predicted $k_A$ values were calculated by equation 1.

Simulations: Concentration-time profiles for single dose were simulated using the following equation:

$$\text{Concentration} = \frac{k_A \cdot \text{Dose} \cdot F}{(k_A - k_E)V} (\exp(-k_E \cdot \text{time}) - \exp(-k_A \cdot \text{time})) \quad (4)$$

where F=bioavailability, F/V=0.625/L, dose=40 mg, and $k_E$=0.274 hour$^{-1}$. Simulated concentrations were normalized so that the Cmax value for CR1 (16.2 ng/mL) was given the relative concentration value of 100. Dissolution studies indicated a lag-time (time preceding the first quantifiable concentration) that increased in the order CR3<CR4<CR5. A similar trend in absorption lag-time (time between dose administration and apparent start of absorption) was observed. There was no observable dissolution lag-time for CR8, CR9, and CR10. For this series of simulations, it was assumed that the lag-time is equal to zero.

Figure 11:
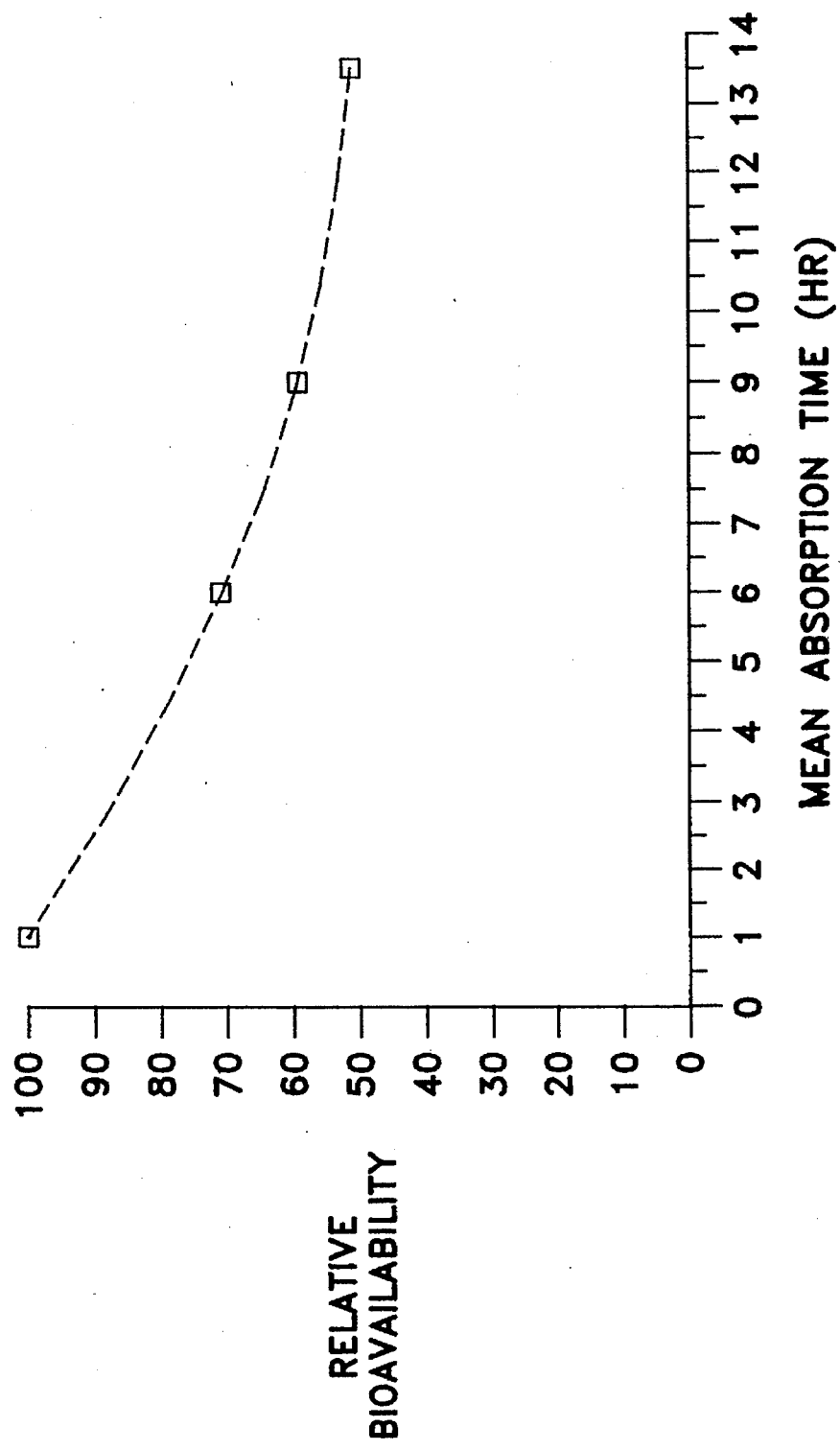
FIG. 11 is a graph showing the simulated Frel as a function of MAT for tacrine formulations (CR1, CR3, CR4, and CR5). Points are connected via a spline function.

Mean AUC from time zero to time of last detectable concentration, AUC(0-tldc), were used as the measure of oral bioavailability. Relative bioavailability ($F_{rel}$) was expressed as percentage of the mean AUC(0-tldc) for CR1. Predicted $F_{rel}$ values for CR8, CR9, and CR10 were determined by inspection from the relationship shown in FIG. 11. It was assumed that the 50% higher loading did not alter this relationship.

Results and Discussion

Wagner-Nelson plots of the amount unabsorbed versus time were log-linear indicating first order absorption. Tacrine absorption ram was characterized by the first order rate constant, $k_A$. Plots of the percentage undissolved versus time were log-linear (FIG. 7) indicating first order release from the CR formulations following a lag phase of 0 to 2 hours. Tacrine dissolution rate was characterized by the first order in vitro rate constant, $k_D$. Formulation $k_A$ and $k_D$ values and the corresponding MAT and MDT values are summarized in the Table 9.

TABLE 9

| Formulation | $k_D$ (1/hr) | MDT (hr) | $k_A$ (1/hr) | MAT (hr) | $F_{rel}$ (%) |
|---|---|---|---|---|---|
| CR1 | 16.9 | 0.06 | 1.21 | 0.83 | 100 |
| CR3 | 0.523 | 1.9 | 0.174 | 5.7 | 69 |
| CR4 | 0.287 | 3.5 | 0.110 | 9.1 | 57 |
| CR5 | 0.192 | 5.2 | 0.074 | 13.5 | 49 |
| CR10 | 1.77 | 0.57 | (0.457)[a] | (2.2) | (91) |
| CR9 | 0.686 | 1.5 | (0.225) | (4.5) | (75) |
| CR8 | 0.442 | 2.3 | (0.156) | (6.4) | (67) |

[a]Values in parenthesis are predicted values.
$k_D$ = Dissolution rate constant (1/hour)
MDT = Mean dissolution time (hour)
$k_A$ = Absorption rate constant (1/hour)
MAT = Mean absorption time (hour)
$F_{rel}$ = Mean AUC (0-tldc) value expressed as percentage of mean value for CR1 as reported previously.

Figure 8:
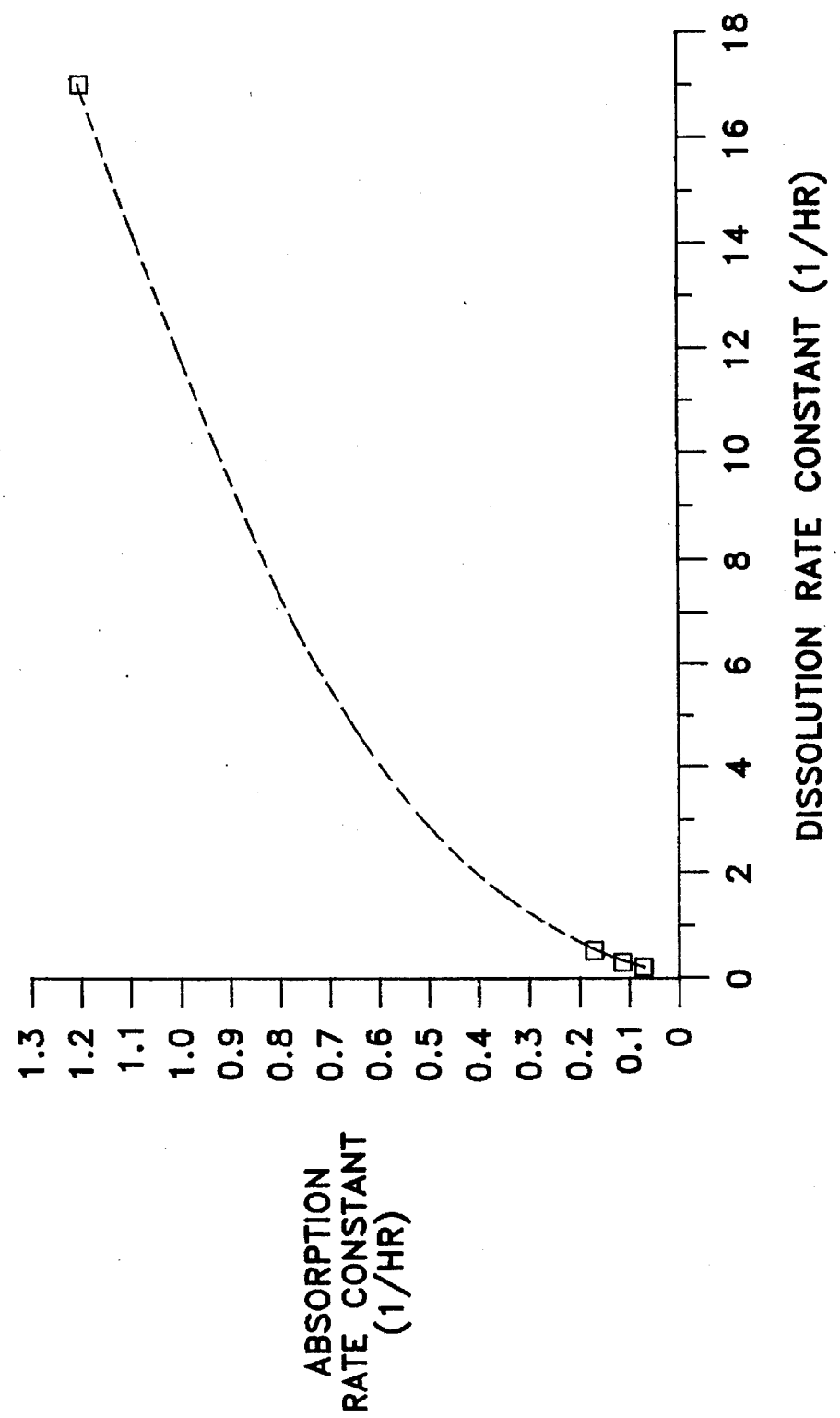
FIG. 8 is a graph showing the average absorption rate constant as a function of dissolution rate constant for tacrine formulations (CR1, CR3, CR4, and CR5). Points are connected via a spline function. A least-squares linear regression line through date for CR1, CR3, CR4, and CR5 is shown in the insert.

In vitro/in vivo correlation: The curvilinear relationship between kA and kD is shown in FIG. 8. This relationship can be approximated as linear over the limited range defined by values for CR3, CR4, and CR5. The linear relationship between MAT and MDT values (FIG. 9) was defined by the following equation:

$$MAT = 0.80 \text{ hr} + 2.435 * MDT (R^2 = 0.998) \quad (5)$$

Predicted MAT values for the CR8, CR9, and CR10 based on Equation 5 and the corresponding $k_A$ values are shown in the table above as parenthetical values.

Results suggest that tacrine absorption from CR10 will be rapid; the larger $k_A$ value the faster the expected absorption rate. Tacrine absorption from CR8 is predicted to be similar to that observed from CR3. Absorption from CR9 will be faster than from CR3. Absorption from CR8 and CR9 is predicted to be dissolution-ram limited because $k_A < k_E$. Deviations from predicted values may result from the difference in tacrine loading of the pellet core.

Figure 10:
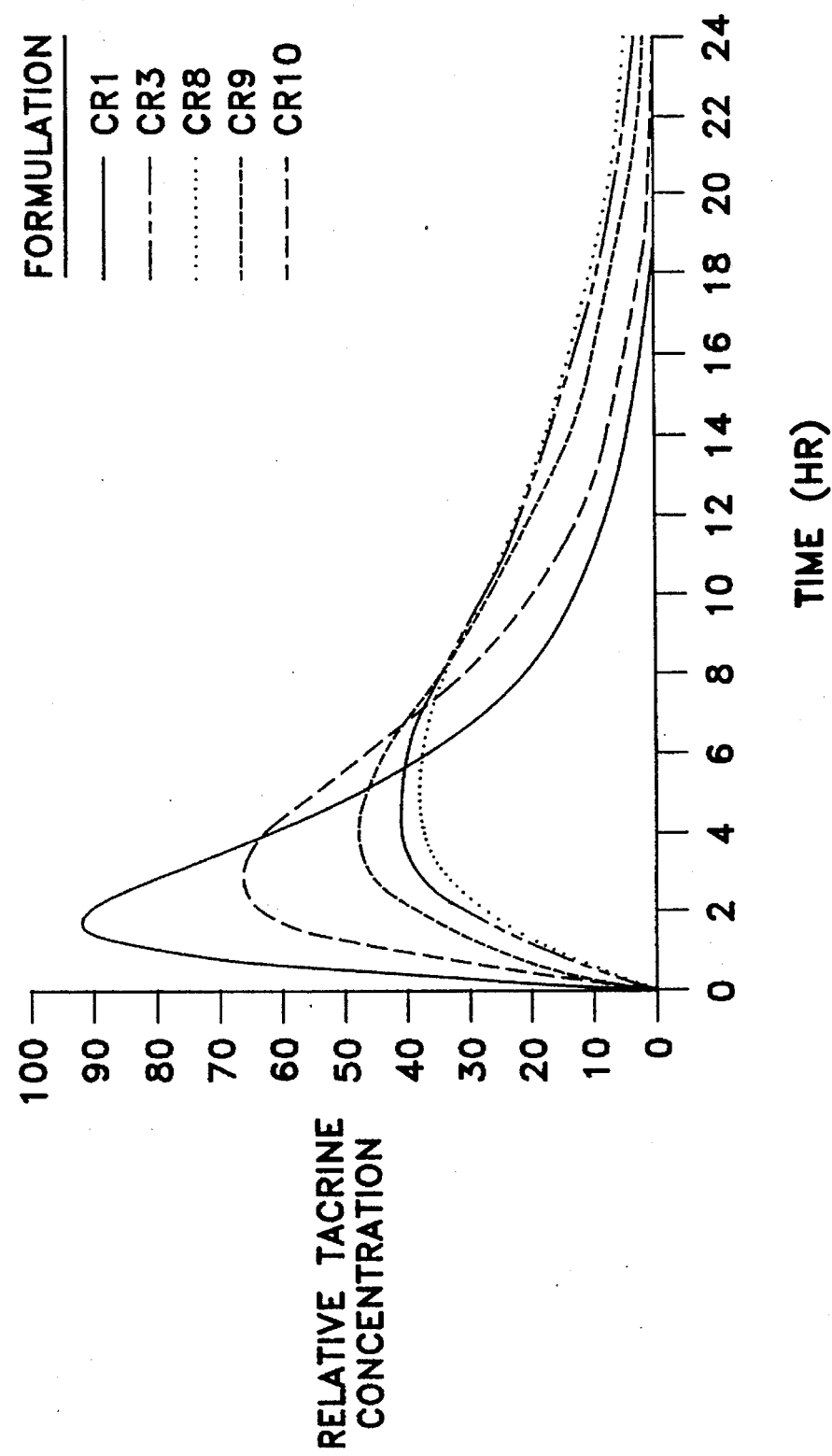
FIG. 10 is a graph showing the simulated plasma tacrine concentrations (CR1, CR3, CRS, CR9, and CR10). Top: linear scale; Bottom: semi-logarithmic scale.

Assuming that the new formulations have the same bioavailability and that the lag-time for absorption is zero, plasma concentrations (Cp) following single doses were simulated by means of equation 4, FIG. 10. These simulations which indicate relative, not absolute Cp values, are useful for comparisons of the shape of the time course for each formulation. Simulations indicate that concentration-time profiles for the new formulations will be different from each other. As absorption rate decreases (decreasing $k_A$ values), Cmax decreases, and concentrations at times >8 hours tend to increase.

Figure 7:
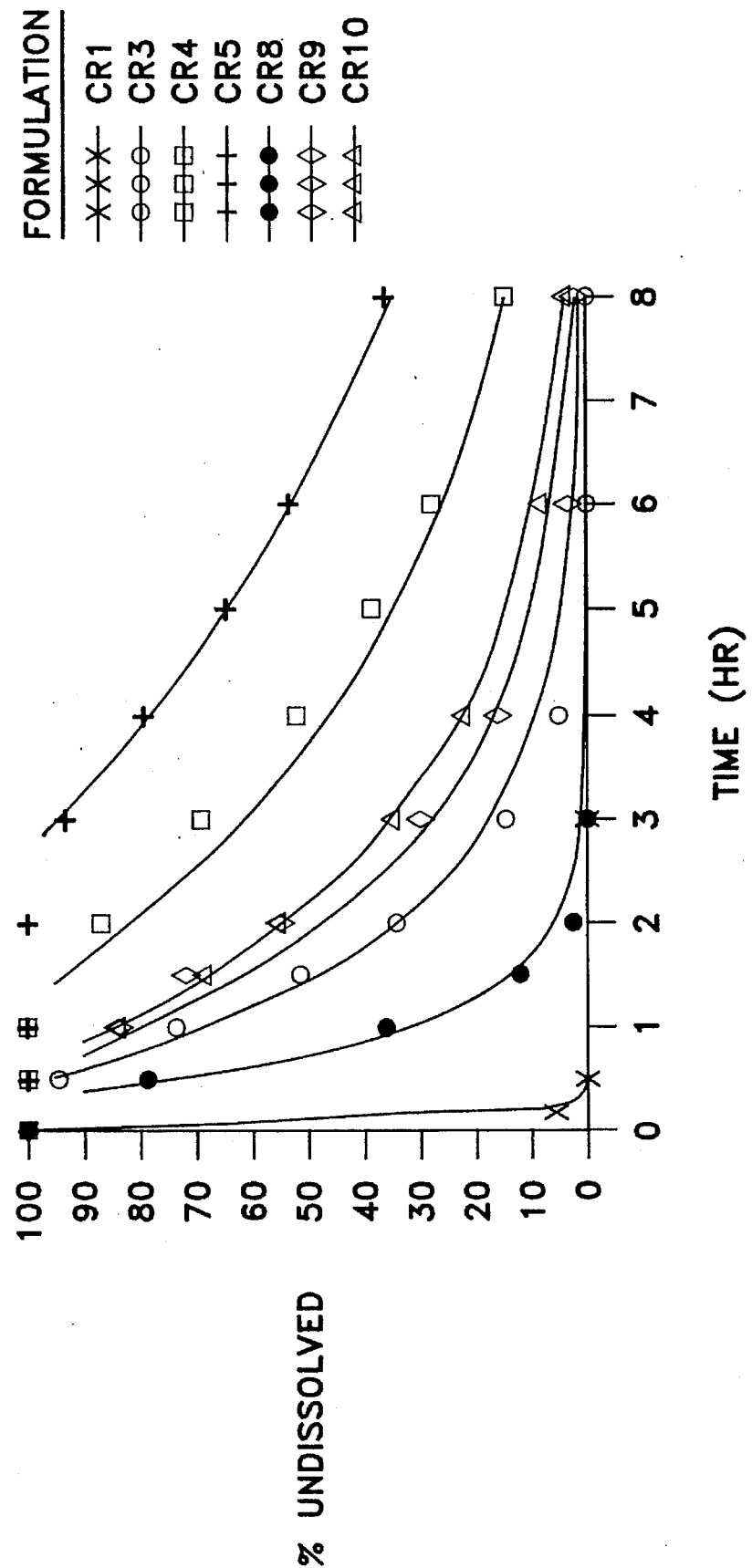
FIG. 7 is a graph showing the percent of dose undissolved as a function of time for seven tacrine formulations (CR1, CR3, CR4, CR5, CR8, CR9, and CR10). Symbols: Observed date; Solid Lines; fitted date to equation 2. Top: linear scale; Bottom: semi-logarithmic scale.
Figure 12:
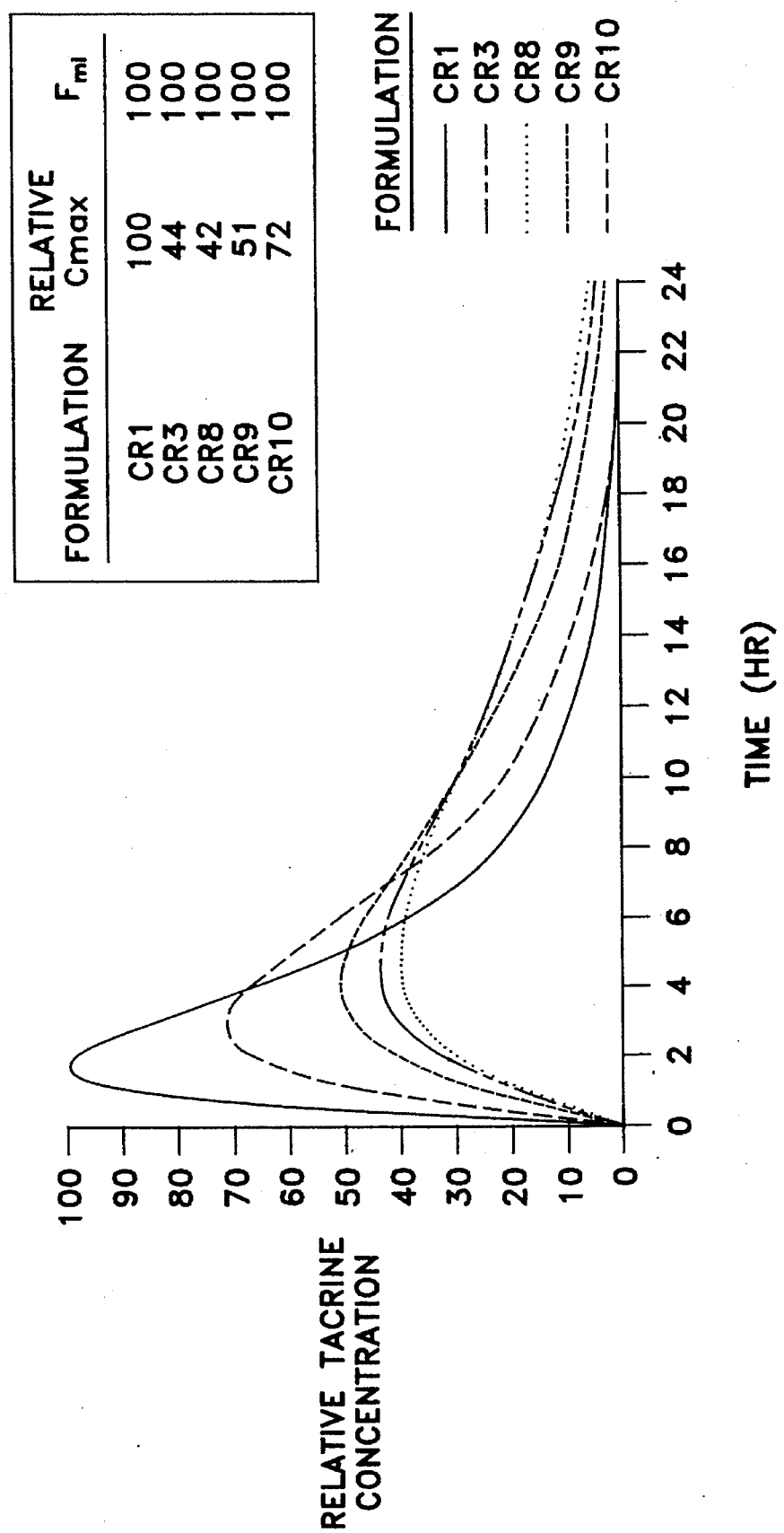
FIG. 12 is a graph showing the simulated plasma tacrine concentrations (CR1, CR3, CRS, CR9, and CR10). Top: 100% relative bioavailability (from FIG. 6); Bottom: bioavailability adjusted according to FIG. 7.
Figure 12A:
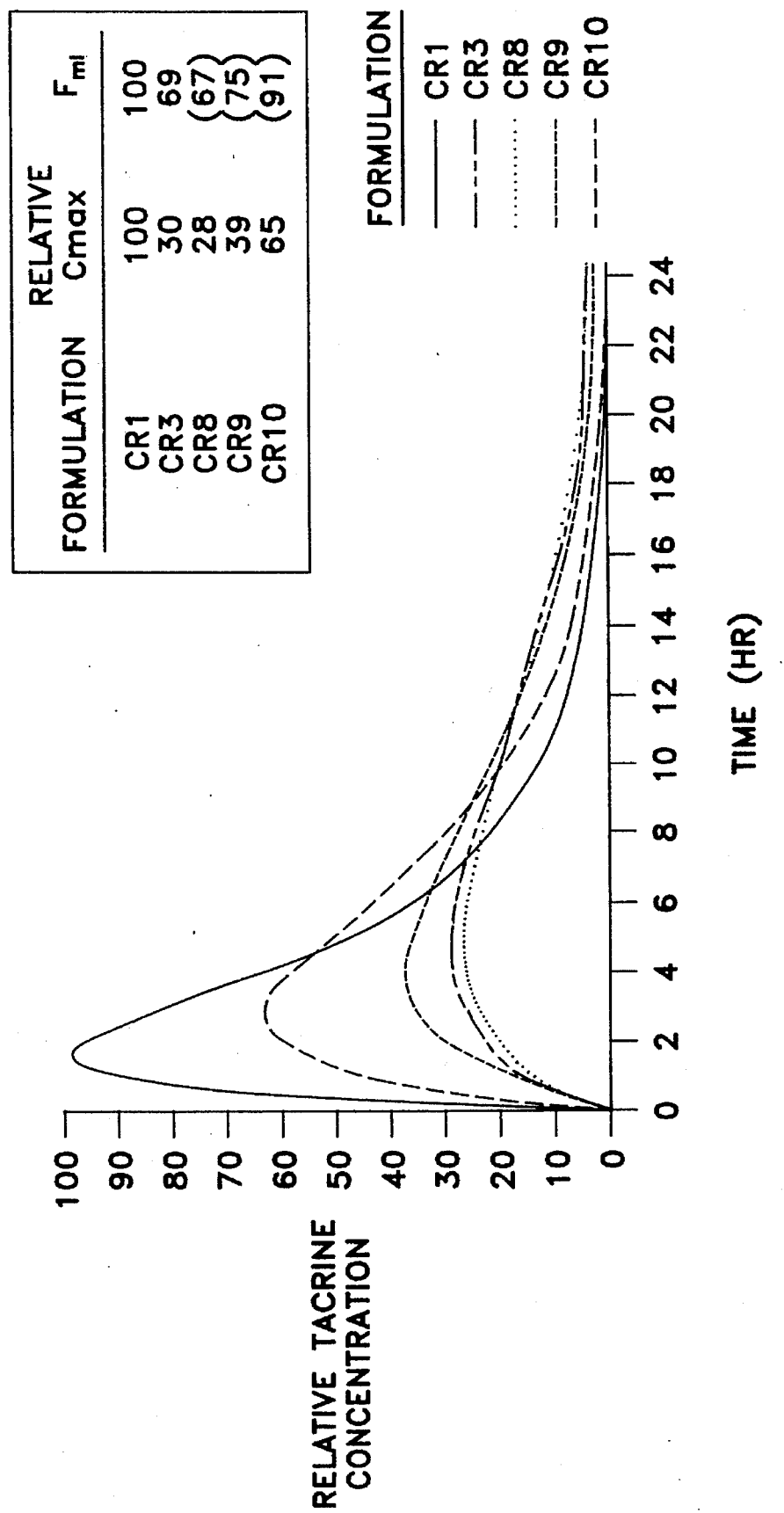

Bioavailability: Results indicated that $F_{rel}$ and absorption rate is curvilinear (FIG. 7); $F_{rel}$ decreases as MAT increases. Decreasing bioavailability with decreasing absorption rate is consistent with nonlinear first pass metabolism. The relationship between $F_{rel}$ and MAT for CR8 will be similar to that for CR3, while that for CR9 and CR10 will be higher. All new formulations are expected to have lower bioavailability than CR1. The effect of $F_{rel}$ on the concentration-time profile following single doses is simulated in FIG. 12 which compares the profiles of the formulations taking into account $F_{rel}$ predicted in FIG. 7. Simulations indicate that the 12 hour plasma levels for CR3, CR5, and CR9 will be very similar, with CR9 having the highest $F_{rel}$ of these three formulations.

In summary, the reported dissolution data and concentration-time results following single-dose administration of tacrine CR formulations indicate that tacrine dissolution and absorption are first order processes. There is a strong positive correlation between mean dissolution time (in vitro) and mean absorption time (in vivo). Simulations for single doses based on the correlation and the relationship between relative bioavailability and absorption ram indicate pharmacokinetics of prototype CR8 will be similar to previously reported values for CR3. Prototypes CR9 and CR10 are predicted to have higher bioavailability and higher Cmax values than reported for CR3, and will retain sustained-release properties relative to the immediate release formulation.

The invention being thus described, it will be obvious that the same may be varied in many ways. Such variations are not to be regarded as a departure from the spirit and scope of the invention and all such modifications are intended to be included within the scope of the following claims.

We claim:

1. A controlled release tacrine drug delivery system comprising an immediate release composition and a sustained release composition, the immediate release and sustained release compositions being prepared from aqueous systems, wherein:

(1) the immediate release composition comprises in percentages by weight of the immediate release composition:

(A) immediate release pellets comprising:
(a) nonpareil seeds in an amount from about 25% to about 75%;
(b) tacrine in an amount from about 10% to about 80%; and
(c) a binding agent in an amount from about 1% to about 10%; and (B) a sealing layer over the immediate release pellets comprising:
(a) a sealing agent that is an alkyl cellulose derivative in an amount up to about 6%, and
(b) a first plasticizing agent in an amount up to about 5%; and (2) the sustained release composition comprises in percentages by weight of the sustained release composition;

(A) the immediate release composition; and
(B) a sustaining layer over the immediate release composition comprising;
(a) a water-insoluble polymer in an amount from about 40% to about 90%;

(b) a water-soluble polymer in an amount up to about 10%; and (c) a second plasticizing agent in an amount up to about 10%; wherein the sustaining layer and the immediate release composition are present in the sustained release composition in a ratio by weight from about 1:9 to about 4:6, respectively, and the immediate release composition and the sustained release composition are present in the drug delivery system in a ratio by weight from about 0.01:1 to about 1:1, respectively, the dissolution rate of tacrine being at least 25% after two (2) hours and at least 50% after six (6) hours when measured in vitro in a type 2 dissolution apparatus according to United States Pharmacopeia.

2. The drug delivery system according to claim 1, wherein tacrine is present in the immediate release composition in an amount from about 15% to about 60%, by weight.

3. The drug delivery system according to claim 1, wherein the binding agent is present in the immediate release composition in an amount from about 2% to about 8%, by weight.

4. The drug delivery system according to claim 1, wherein the binding agent in the immediate release composition is povidone.

5. The drug delivery system according to claim 1, wherein the sealing agent is present in the immediate release composition in an amount up to about 4%, by weight.

6. The drug delivery system according to claim 1, wherein the sealing agent in the immediate release composition is hydroxypropyl methylcellulose.

7. The drug delivery system according to claim 1, wherein the first plasticizing agent in the immediate release composition is polyethylene glycol.

8. The drug delivery system according to claim 1, wherein the immediate release composition further comprises an antiadherent.

9. The drug delivery system according to claim 1, wherein the water-insoluble polymer is present in the sustained release composition in an amount from about 45% to about 85%, by weight.

10. The drug delivery system according to claim 9, wherein the water-insoluble polymer is present in the sustained release composition in an amount from about 50% to about 80%, by weight.

11. The drug delivery system according to claim 1, wherein the water-insoluble polymer in the sustained release composition is ethylcellulose.

12. The drug delivery system according to claim 1, wherein the water-soluble polymer is present in the sustained release composition in an amount up to about 10%, by weight.

13. The drug delivery system according to claim 12, wherein the water-soluble polymer is present in the sustained release composition in an amount up to about 5%, by weight.

14. The drug delivery system according to claim 1, wherein the water-soluble polymer in the sustained release composition is hydroxypropyl methylcellulose.

15. The drug delivery system according to claim 1, wherein the second plasticizing agent in the sustained release composition is triethyl citrate.

16. The drug delivery system according to claim 1, wherein the sustaining layer and the immediate release composition are present in the sustained release composition in a ratio by weight from about 1:9 to about 3:7, respectively.

17. The drug delivery system according to claim 16, wherein the sustaining layer and the immediate release composition are present in the sustained release composition in a ratio by weight from about 1:9 to about 2:8, respectively.

18. The drug delivery system according to claim 1, wherein the immediate release composition and the sustained release composition are present in the drug delivery system in a ratio by weight from about 1:9 to about 2:8, respectively.

19. The drug delivery system according to claim 18, wherein the immediate release composition and the sustained release composition are present in the drug delivery system in a ratio by weight from about 2:8 to about 4:6, respectively.

20. A method for preparing a controlled release tacrine drug delivery system comprising an immediate release composition and a sustained release composition, which comprises the steps of:

(i) providing the following ingredients:

(1) the immediate release composition comprises in percentages by weight of the immediate release composition:

(A) immediate release pellets comprising:

(a) nonpareil seeds in an amount from about 25% to about 75%;

(b) tacrine in an amount from about 10% to about 80%; and (c) a binding agent in an amount from about 1% to about 10%; and (B) a sealing layer over the immediate release pellets comprising:

(a) a sealing agent that is an alkyl cellulose derivative in an amount up to about 6%, and (b) a first plasticizing agent in an amount up to about 5%; and (2) the sustained release composition comprises in percentages by weight of the sustained release composition;

(A) the immediate release composition; and (B) a sustaining layer over the immediate release composition comprising;

(a) a water-insoluble polymer in an amount from about 40% to about 90%;

(b) a water-soluble polymer in an amount up to about 10%; and (c) a second plasticizing agent in an amount up to about 10%;

wherein the sustaining layer and the immediate release composition are present in the sustained release composition in a ratio by weight from about 1:9 to about 4:6, respectively, and the immediate release composition and the sustained release composition are present in the drug delivery system in a ratio by weight from about 0.01:1 to about 1:1, respectively;

(ii) forming an aqueous suspension of the tacrine and the binding agent from step (i)(1)(A) and layering the suspension on the nonpareil seeds to form immediate release pellets;

(iii) forming an aqueous mixture of the sealing agent and first plasticizing agent from step (i)(1)(B) and coating the immediate release pellets to form the immediate release composition;

(iv) forming an aqueous dispersion of the water-insoluble polymer, water-soluble polymer, and second plasticizing agent from step (i)(2)(B) and coating a portion of the immediate release composition to form the sustained release composition; and (v) admixing the immediate release composition and the sustained release composition in a ratio by weight from about 0.01:1 to about 1:1, respectively, to form the controlled release tacrine drug delivery system, the dissolution rate of tacrine being at least 25% after two (2) hours and at least 50% after six (6) hours when measured in vitro in a type 2 dissolution apparatus according to United States Pharmacopeia.

* * * * *